(12) United States Patent
Trowell et al.

(10) Patent No.: US 10,101,319 B2
(45) Date of Patent: Oct. 16, 2018

(54) METHODS OF DETECTING PLASMODIUM INFECTION

(71) Applicant: Commonwealth Scientific and Industrial Research Organisation, Acton, ACT (AU)

(72) Inventors: Stephen Trowell, Oxley (AU); Amalia Berna, Macgregor (AU); Benjamin Padovan, Kambah (AU); Vicki Locke, O'Connor (AU)

(73) Assignee: Commonwealth Scientific and Industrial Research Organisation, Acton, ACT (AU)

( * ) Notice: Subject to any disclaimer, the term of this patent is extended or adjusted under 35 U.S.C. 154(b) by 0 days.

(21) Appl. No.: 15/039,806

(22) PCT Filed: Nov. 28, 2014

(86) PCT No.: PCT/AU2014/050384
§ 371 (c)(1),
(2) Date: May 26, 2016

(87) PCT Pub. No.: WO2015/077843
PCT Pub. Date: Jun. 4, 2015

(65) Prior Publication Data
US 2017/0045495 A1    Feb. 16, 2017

(30) Foreign Application Priority Data
Nov. 28, 2013   (AU) ................................ 2013904616

(51) Int. Cl.
*G01N 33/497* (2006.01)
*C12Q 1/04* (2006.01)
(Continued)

(52) U.S. Cl.
CPC .......... *G01N 33/497* (2013.01); *A61B 5/082* (2013.01); *C12Q 1/04* (2013.01); *C12Q 1/18* (2013.01);
(Continued)

(58) Field of Classification Search
CPC .. G01N 33/497; G01N 33/50; G01N 2800/52; G01N 2560/00; G01N 2800/26;
(Continued)

(56) References Cited

U.S. PATENT DOCUMENTS

2001/0026915 A1   10/2001   Charych et al.

FOREIGN PATENT DOCUMENTS

WO   WO 2004057333   7/2004
WO   WO 2010085844   8/2010
(Continued)

OTHER PUBLICATIONS

Wong et al., (Malar J. Sep. 7, 2012;11:314.).*
(Continued)

*Primary Examiner* — Jana A Hines
(74) *Attorney, Agent, or Firm* — Michael B. Rubin; Bozicevic, Field & Francis LLP

(57) ABSTRACT

The present invention relates to a method of identifying a subject with a *Plasmodium* infection. The present invention also relates to a method for monitoring a subject with a *Plasmodium* infection, for example, following treatment with an anti-malaria compound. Also provided are methods of identifying a compound to treat a *Plasmodium* infection.

8 Claims, 23 Drawing Sheets

Figure 1:
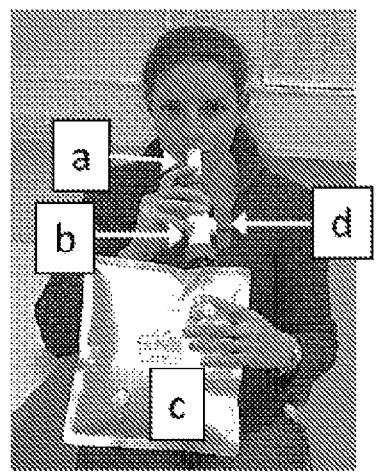

(51) Int. Cl.
*A61B 5/08* (2006.01)
*C12Q 1/18* (2006.01)
*G01N 33/50* (2006.01)
*A61B 5/00* (2006.01)

(52) U.S. Cl.
CPC ..... G01N 33/5082 (2013.01); G01N 33/5088 (2013.01); *A61B 5/4244* (2013.01); *A61B 5/4848* (2013.01); *G01N 2033/4975* (2013.01); *G01N 2333/445* (2013.01); *G01N 2560/00* (2013.01); *G01N 2800/26* (2013.01); *G01N 2800/52* (2013.01)

(58) Field of Classification Search
CPC ........ G01N 33/5082; C12Q 1/44; C12Q 1/02; C12Q 1/32; C12Q 1/04; C12M 1/00; A61B 5/4244; A61B 5/4848; A61B 5/082
USPC ........................... 435/7.92, 19, 26, 29, 287.1
See application file for complete search history.

(56) References Cited

FOREIGN PATENT DOCUMENTS

| WO | WO 2013155553 | 10/2013 |
|----|---------------|---------|
| WO | WO 2013163610 | 10/2013 |

OTHER PUBLICATIONS

Penny, et al (2006) "Biomarkers for Infectious Disease Diagnostics in the Developing World: Rapid, Home-based Diagnosis of Malaria in Symptomatic Individuals and Screening of Asymptomatic Pregnant Women"; Halteres Associates LLC; pp. 1-41.
Extended European Search Report for European Patent Application No. 14866453.5, dated Jun. 21, 2017.
Aregawi et al. (2011) World Health Organization, Global Malaria Programme. World Malaria Report 2011, Geneva, World Health Organization.
Biamonte et al. (2013) "Recent advances in malaria drug discovery"; Bioorganic & Medicinal Chemistry Letter& 23; pp. 2829-2843.
Bloland (2001) "Drug resistance in malaria"; WHO/CDS/CSR/DRS/2001.4.
Chang, Chih-Chung and Lin, Chih-Jen, LIBSVM : a library for support vector machines. ACM Transactions on Intelligent Systems and Technology, 2:27:1-27:27, 2011.
Cortes and Vapnik (1995) "Support-vector networks"; Machine Learning vol. 20, Issue 3, pp. 273-297.
Dowell and Brown (2009) "Yeast assays for G protein-coupled receptors"; Methods in Molecular Biology 552; pp. 213-229.
Fukutani et al (2012) "The N-terminal replacement of an olfactory receptor for the development of a yeast-based biomimetic odor sensor"; *Biotechnol Bioeng.* 109(1); pp. 205-212.
Hanscheid (1999) "Diagnosis of malaria: a review of alternatives to conventional microscopy"; *Clin Lab Haematol.* 21(4); 235-245.
Karunamoorthi (2014) "The counterfeit anti-malarial is a crime against humanity: a systematic review of the scientific evidence"; Malaria Journal 13:209; pp. 1-13.
Le Manach et al (2013) "Fast in vitro methods to determine the speed of action and the stage-specificity of anti-malarials in Plasmodium falciparum"; Malaria Joumal 12:424; pp. 1-7.
McCarthy et al (2011) "A Pilot Randomised Trial of Induced Blood-Stage Plasmodium falciparum Infections in Healthy Volunteers for Testing Efficacy of New Antimalarial Drugs"; PLoS One. 6(8):e21914. doi: 10.1371/journal.pone.0021914.
McCarthy et al. (2013) "Experimentally induced blood-stage Plasmodium vivax infection in healthy volunteers"; J Infect Dis. 208(10); 1688-94. doi: 10.1093/infdis/jit394.
Mochalski et al. (2013) "Blood and breath levels of selected volatile organic compounds in healthy volunteers"; Analyst.138(7); pp. 2134-2145.
Vaughan et al. (2012) "Development of humanized mouse models to study human malaria parasite infection"; Future Microbial. 7(5); pp. 657-665.
Wang et al (2014) "Feature selection for chemical sensor arrays using mutual information"; PLoS One 9(3):e89840.
Wilson Michael L. (2012) "Malaria rapid diagnostic tests"; Clinical Infectious Diseases 54(11); pp. 1637-1641.
Wong et al (2012) "Investigation of volatile organic biomarkers derived from Plasmodium falciparum in vitro"; Malaria Journal 11:314.

\* cited by examiner

METHODS OF DETECTING PLASMODIUM INFECTION

FIELD OF THE INVENTION

The present invention relates to a method of identifying a subject with a *Plasmodium* infection. The present invention also relates to a method for monitoring a subject with a *Plasmodium* infection, for example, following treatment with an anti-malaria compound. Also provided are methods of identifying a compound to treat a *Plasmodium* infection.

BACKGROUND OF THE INVENTION

*Plasmodium* spp. are parasitic protozoa and the human infection caused by these organisms is known as malaria. Malaria is a devastating infectious disease. There are over 300 million cases per year worldwide and resulting in approximately 660,000 million deaths per year. *Plasmodium* species that infect humans are transmitted by the bite of an infected Anopheline mosquito. *Plasmodium falciparum* is responsible for most of the deaths due to malaria. However, *Plasmodium vivax* is the most prevalent species worldwide and causes a significant amount of morbidity. *Plasmodium falciparum*, the cause of the most virulent form of malaria, has developed resistance to currently used drugs. This in turn has led to an increase in the incidence of malaria and to fewer drugs for both treatment and prophylaxis of the disease. Other species of *Plasmodium*, such as *P. knowlesi* and *P. ovale*, although they principally infect other animals, may also cause disease in humans.

Malaria infection is initiated when an infected Anopheline mosquito injects sporozoites into a subject during the mosquito's blood meal. After injection, the parasite enters the bloodstream and undergoes a series of changes as part of its lifecycle. The sporozoite travels to the liver where it invades hepatocytes. One sporozoite can generate over 10,000 merozoites which will then rupture from the hepatocyte and invade erythrocytes, although *P. vivax* and *P. ovale* can remain dormant in the liver (hypnozoites) and cause relapses years after the initial infection. In their intraerythrocyte phase, the merozoites go through various forms (rings, trophozoites, schizonts) to form an average of 20 daughter merozoites that are released into the bloodstream and infect new red blood cells (Biamonte et al., 2013). This causes the symptomatic high fevers and associated pathology.

The disease malaria is usually confirmed by the microscopic examination of blood films or by antigen-based rapid diagnostic tests (RDT). Microscopy is the most commonly used method to detect the malarial parasite—about 165 million blood films were examined for malaria in 2010 (Aregawi et al., 2011). Despite its widespread usage, diagnosis by microscopy suffers from two main drawbacks: many settings (especially rural) are not equipped to perform the test, and the accuracy of the results depends on both the skill of the person examining the blood film and the levels of the parasite in the blood. The sensitivity of blood films ranges from 75-90% in optimum conditions, to as low as 50%. Commercially available RDTs may be more accurate than blood films at predicting the presence of malaria parasites, but they are widely variable in diagnostic sensitivity and specificity depending on manufacturer, and are unable to tell how many parasites are present (Wilson, 2012).

Antimalarial drug resistance has emerged as one of the greatest challenges facing malaria control today. Drug resistance has been implicated in the spread of malaria to new areas and re-emergence of malaria in areas where the disease had been eradicated. Drug resistance has also played a significant role in the occurrence and severity of epidemics in some parts of the world (Bloland, 2001). Unfortunately, current techniques to detect resistance, such as PCR analysis, require several weeks to be completed.

There is a need to provide faster, cheaper and non-invasive ways to detect *Plasmodium* infection in particular low levels of infection presented in children in pregnant women and to monitor the effectiveness of treatment, especially in the face of drug-resistant strains of *Plasmodium* spp. There is also the need for new ways of screening for compounds to treat *Plasmodium* infection.

SUMMARY OF THE INVENTION

The present inventors have identified new markers which can be used to identify and monitor *Plasmodium* infection in a subject.

In one aspect, the present invention provides a method for identifying a subject with a *Plasmodium* infection, the method comprising detecting one or more volatile organic compounds selected from the group consisting of allyl methyl sulphide, 1-methylthiopropane, (E)-1-methylthio-1-propene, and (Z)-1-methylthio-1-propene, in the subject or a sample obtained therefrom, wherein the levels of the one or more volatile organic compounds indicates a *Plasmodium* infection.

In an embodiment, the levels of the one or more volatile organic compounds also indicate the status of the *Plasmodium* infection.

In another aspect, the present invention provides a method for monitoring a subject with a *Plasmodium* infection, the method comprising detecting one or more volatile organic compounds selected from the group consisting of allyl methyl sulphide, 1-methylthiopropane, (E)-1-methylthio-1-propene, and (Z)-1-methylthio-1-propene, in the subject or a sample obtained therefrom, wherein the subject is previously known to have a *Plasmodium* infection, and wherein the levels of the one or more volatile organic compounds is indicative of the status of the *Plasmodium* infection.

The subject can be monitored following being administered with a compound to treat the infection. This allows for it to be determined whether the treatment has been effective, and if not the subject can undergo further or modified treatment and/or monitoring.

The inventors have found that a short time after being administered with a compound to treat the infection the levels of the one or more volatile organic compounds increase before returning to around normal (healthy) levels, with the most prominent increase being with (Z)-1-methylthio-1-propene. Without wishing to be limited by theory, this may be the result of *Plasmodium* cell death. Thus, in an embodiment, an initial increase in the level of the one or more volatile organic compounds after the treatment, when compared to the levels before the treatment, indicates that the treatment is being effective. In an embodiment, the initial increase is monitored at least by detecting the level of (Z)-1-methylthio-1-propene.

In one embodiment of the method for monitoring a subject with a *Plasmodium* infection, the subject is monitored for the initial increase between 0.5 and 72 hours after being administered with the treatment.

In another embodiment of the method for monitoring a subject with a *Plasmodium* infection, a reduction in the levels of one or more volatile organic compounds indicates that the treatment has been effective. In an embodiment, effective treatment of the infection is monitored at least by detecting the level of (E)-1-methylthio-1-propene.

In a further embodiment, the reduction in the levels of one or more volatile organic compounds is after the initial increase in the levels of one or more volatile organic compounds.

Since the levels of the one or more volatile organic compounds can be used to indicate the status of the *Plasmodium* infection this allows the determination of the levels to be used to select a suitable treatment for the infection. Thus, in another aspect the present invention provides a method of selecting a suitable treatment for a *Plasmodium* infection, the method comprising detecting the level of one or more volatile organic compounds selected from the group consisting of allyl methyl sulphide, 1-methylthiopropane, (E)-1-methylthio-1-propene, and (Z)-1-methylthio-1-propene, in the subject or a sample obtained therefrom, and selecting a suitable treatment based on the level of the one or more volatile organic compounds.

Examples of suitable samples include, but are not necessarily limited to, exhaled breath, condensate breath, saliva, blood, sweat, skin microbiota, skin volatile sample and urine. In an embodiment, the sample is exhaled breath. In another embodiment, the sample is exhaled breath where alveolar air is excluded.

In one embodiment, a method of the invention further comprises comparing the level of the one or more volatile organic compounds to a suitable control. For instance when identifying a *Plasmodium* infection the control may be the same type of sample (for example exhaled breath) obtained from an individual known not to be infected with *Plasmodium*. In another example, when monitoring a subject with a *Plasmodium* infection the control may be the same type of sample (for example exhaled breath) obtained from the subject before treatment with a compound to treat the infection. In one example, the exhaled breath of a subject excludes alveolar air.

The subject may be any species which can be infected by *Plasmodium*. In an embodiment the subject is an animal, preferably a mammal. The animal may be human or non-human animal. For example, the subject may be selected from a bird, rat, mouse, primate, non-human primate (NHP) and a human. In some embodiments, the animal may be a humanized animal, such as the humanized mouse or rat. In one embodiment, the subject is human.

The one or more volatile organic compounds can also be used in methods of screening for new anti-malarial compounds. Thus, in another aspect the present invention provides a method of identifying a compound to treat a *Plasmodium* infection, the method comprising:

i) administering a candidate compound to a subject infected with *Plasmodium*; and ii) monitoring the subject or a sample obtained therefrom for the levels of one or more volatile organic compounds selected from the group consisting of allyl methyl sulphide, 1-methylthiopropane, (E)-1-methylthio-1-propene, and (Z)-1-methylthio-1-propene;

wherein following step i) an initial increase in the levels of the one or more volatile organic compounds, and/or a reduction in the levels of the one or more volatile organic compounds, indicates that the compound could be used to treat a *Plasmodium* infection.

In one embodiment of the above aspect, the subject is a laboratory animal which is a model organism of malaria. Such model organisms are known in the art and include transgenic humanized mice and rats.

Furthermore, the one or more volatile organic compounds can also be used to identify a strain of *Plasmodium* which has developed resistance to an anti-*Plasmodium* compound. Accordingly, in a further aspect the present invention provides a method of identifying a strain of *Plasmodium* which has developed resistance to an anti-*Plasmodium* compound, the method comprising i) administering the anti-*Plasmodium* compound to a subject infected with a *Plasmodium* strain, and ii) monitoring the subject or a sample obtained therefrom for the levels of one or more volatile organic compounds selected from the group consisting of allyl methyl sulphide, 1-methylthiopropane, (E)-1-methylthio-1-propene, and (Z)-1-methylthio-1-propene, wherein following step i) a lack of a significant change in the levels of the one or more volatile organic compounds indicates that the *Plasmodium* strain has resistance to the anti-*Plasmodium* compound.

In an embodiment of the two above aspects, the method comprises determining the levels of the one or more volatile organic compounds before step i), and comparing these levels to those obtained after step i).

In another embodiment of the two above aspects, the method further comprises before step i):

1) obtaining the subject without a *Plasmodium* infection, and determining the levels of the one or more volatile organic compounds in the subject or a sample obtained therefrom, and 2) infecting the subject with the *Plasmodium* or the *Plasmodium* strain, and determining the levels of the one or more volatile organic compounds in the infected subject or a sample obtained therefrom.

In an embodiment, the method comprises comparing the levels of the one or more volatile organic compounds from steps 1) and/or 2) with the levels of the one or more volatile organic compounds after administering the candidate compound or anti-*Plasmodium* compound.

In yet a further embodiment, the method comprises determining the fold difference in the levels of the one or more volatile organic compounds between one or more of steps 1) and 2) and ii).

The present inventors have identified further, which may be considered as secondary, volatile organic compounds which can be used in the methods of the invention. Thus, in a further embodiment, the methods of the invention further comprise determining the levels of one or more additional volatile organic compounds selected from the group consisting of carbon dioxide, isoprene, acetone, benzene and cyclohexanone.

The one or more volatile organic compounds can be detected/monitored or similar by any technique known in the art. Examples include, but are not limited to, one or more of gas chromatography mass spectrometry (GCMS), liquid chromatography mass spectrometry (LCMS), electronic nose device, biosensor, an antibody-based detection system, colorimetric assays, near-infrared (NIR), selected ion flow tube mass spectrometry (SIFT) and proton transfer reaction mass spectrometry (PTR-MS). In one example, the one or more volatile organic compounds are detected/monitored or similar using gas chromatography mass spectrometry (GCMS) or an electronic nose device.

The one or more volatile organic compounds can be used as reagents to identify compounds (which may be in the form of a composition) which can be used in the methods of the invention, for instance as a sensor compound. Accordingly, in yet a further aspect, the present invention provides a method of screening for a compound for identifying a subject with a *Plasmodium* infection, the method comprising i) contacting a candidate compound with a volatile organic compound selected from the group consisting of allyl methyl sulphide, 1-methylthiopropane, (E)-1-methylthio-1-propene and (Z)-1-methylthio-1-propene, and ii) determining if the compound binds or reacts with the volatile organic compound, wherein a compound which binds or reacts with the volatile organic compound can be used in a method for identifying and/or monitoring a subject with a *Plasmodium* infection of the invention, and/or a method of selecting a suitable treatment of the invention.

The candidate compound could be any type of compound such as a small-carbon based molecule or a protein. In an embodiment, the protein is an antibody or a receptor such as a G protein coupled receptor. In another embodiment, the candidate compound is a solid state sensor composition. For example, the candidate compound is a doped and undoped metal oxide sensor.

The present inventors have identified a sensor compound suitable for detecting the presence of allyl methyl sulfide. In one embodiment, the candidate compound is a metal oxide sensor selected from tin dioxide ($SnO_2$) and tungsten trioxide ($WO_3$), wherein the oxide sensor is optionally doped with a metal selected from the group consisting of palladium (Pd), platinum (Pt), silver (Ag), copper (Cu), or combinations thereof (such as platinum silver compounds (PtAg)). In one embodiment, the candidate compound is tin dioxide doped with silver ($SnO_2$ doped with Ag).

The detection of two, three or four volatile organic compounds can, for example, be any combination of allyl methyl sulphide, 1-methylthiopropane, (E)-1-methylthio-1-propene and (Z)-1-methylthio-1-propene.

One embodiment involves the detection of (Z)-1-methylthio-1-propene, (E)-1-methylthio-1-propene, 1-methylthio propane and allyl methyl sulfide. Another embodiment involves the detection of (Z)-1-methylthio-1-propene, (E)-1-methylthio-1-propene and 1-methylthio propane. Another embodiment involves the detection of (Z)-1-methylthio-1-propene and (E)-1-methylthio-1-propene.

The *Plasmodium* can be any species examples of which include, but are not necessarily limited to, *Plasmodium falciparum, Plasmodium knowlesi, Plasmodium vivax, Plasmodium ovale curtisi, Plasmodium ovale wallikeri* or *Plasmodiun malariae*. In an embodiment, the *Plasmodium* is *Plasmodium falciparum* or *Plasmodium vivax*.

In a further embodiment, if the *Plasmodium* is *Plasmodium vivax* a method of the invention at least comprises detecting the level of (Z)-1-methylthio-1-propene.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1—Picture of breath collection from a volunteer.

Figure 2:
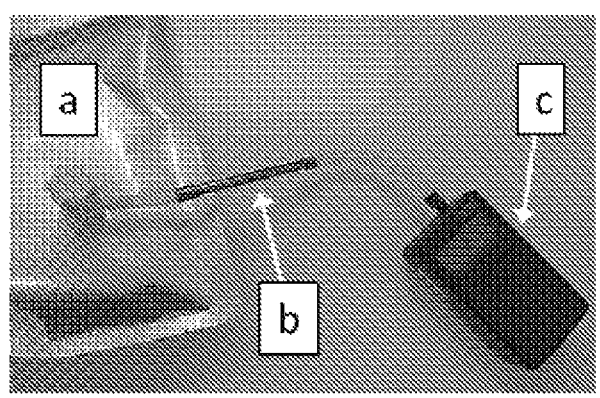

FIG. 2—Picture of transfer of breath volatiles from a breath bag (a) to a sorbent tube (b) using an electric pump (c).

Figure 3:

FIG. 3—Picture of ambient air collection system.

Figure 4:
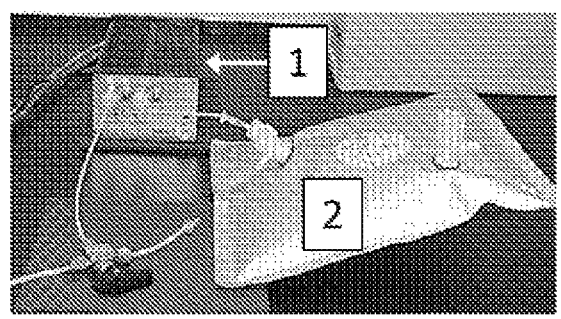

FIG. 4—Picture of direct breath analysis by E-nose (1) made by sampling expired breath directly from breath bags (2).

Figure 5:
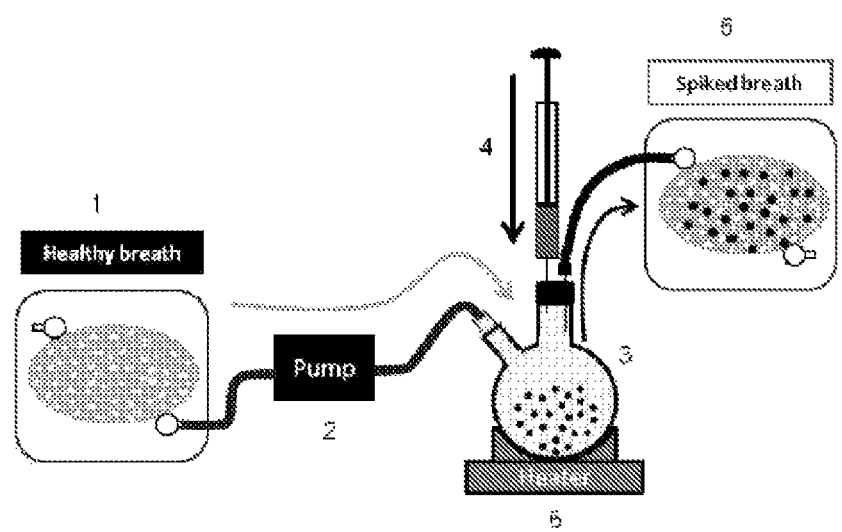

FIG. 5—Schematic diagram for the preparation of spiked breath with malaria biomarker as a patient simulator comprising healthy breath bag (1), micro pump (2), two-neck round bottom boiling flask (3), spiking point (4) "spiked breath" bag (5) and a hot plate heater (6).

Figure 6:
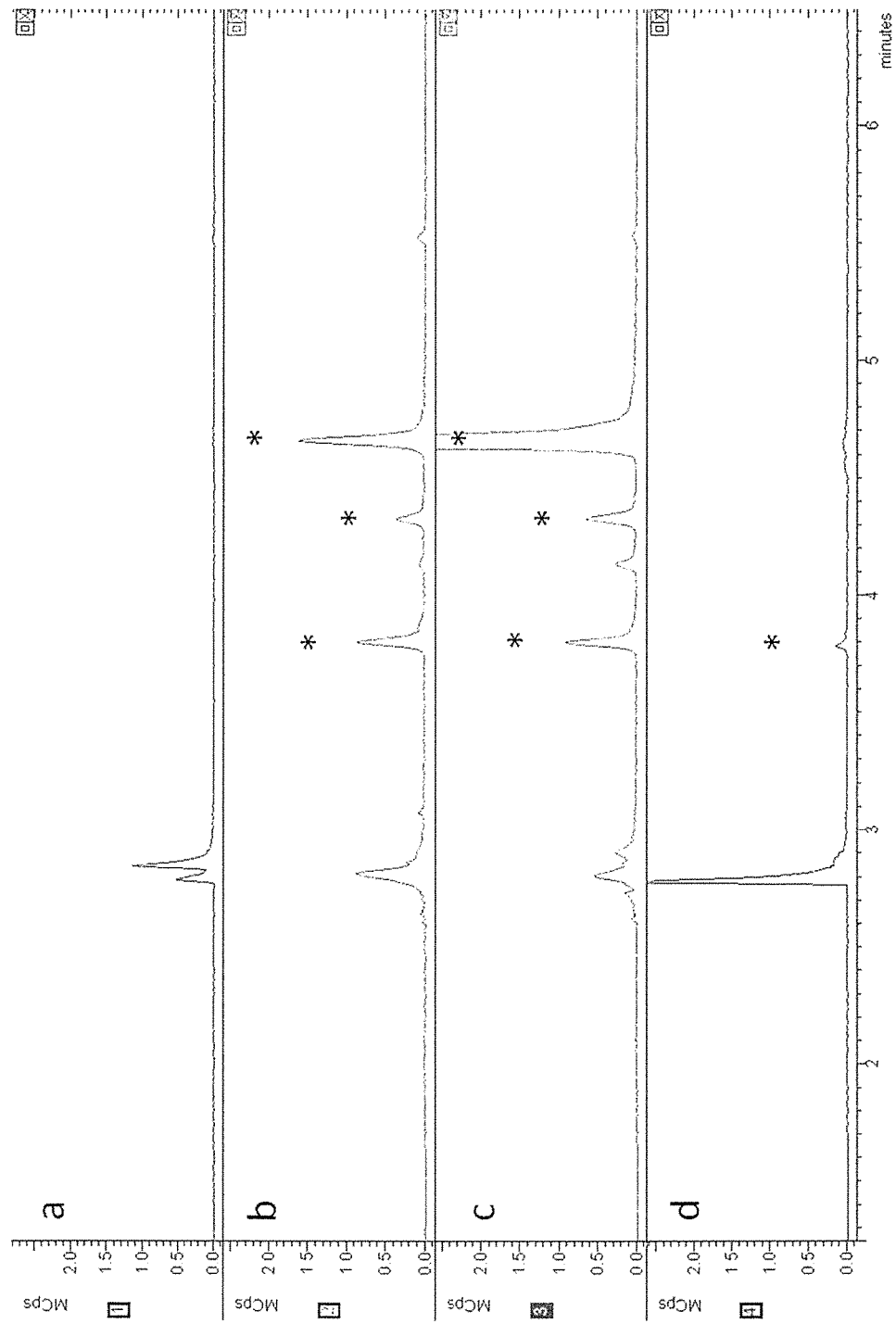

FIG. 6—Single ion (m/z 88) GCMS chromatograms for Cohort 1 showing the first six minutes of analysis time. Chromatogram of sample collected at baseline (Day 0 (a)), chromatogram of sample collected when volunteer was infected with malaria (Day 4 (b)), chromatogram of sample collected soon after anti-malaria was injected (Day7-PM (c)), and chromatogram of sample collected at recovery (Day 28, (d)).

Figure 7:
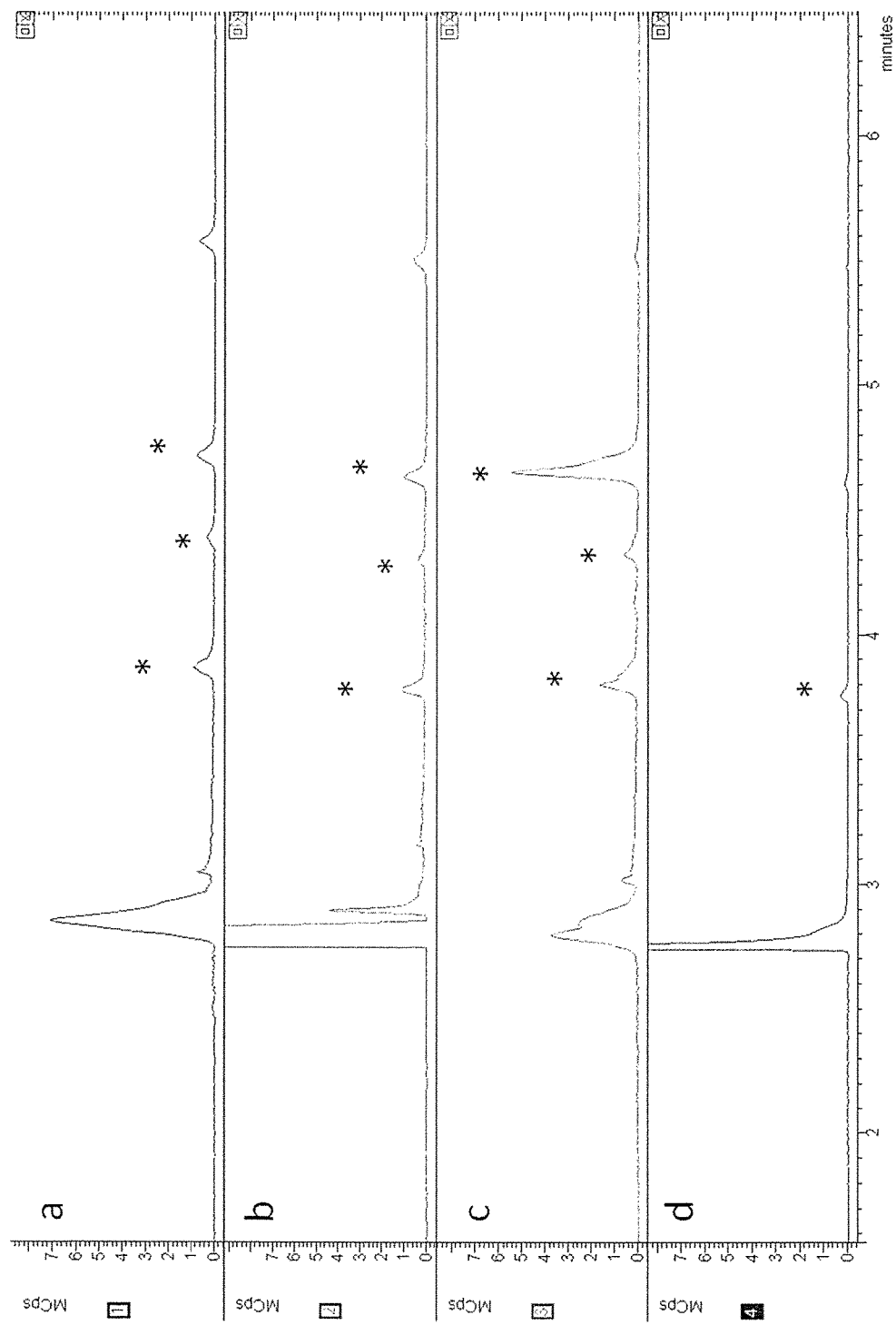

FIG. 7—Single ion (m/z 88) GCMS chromatograms for cohort 2 showing the first six minutes of analysis time at baseline Day 0 (a), when volunteer was infected with malaria Day 4 (b), sample collected soon after anti-malaria was injected Day7-PM (c), and sample collected at recovery Day 28 (d).

FIG. 8—PCA score plot Cohort 1 based on GC-MS data (area under the peak) for four thioethers (allyl methyl sulphide, 1-methylthiopropane, (E)-1-methylthio-1-propene, and (Z)-1-methylthio-1-propene) and breath samples collected at baseline Day 0 (BL) (a), during malaria infection Day 7-AM (If) (b), after anti-malaria administration Day 7-PM (Drug) (c), at recovery phase Day 28 (Rec) (d), and an overlay of PCA score plots FIG. 8*a* to 8*d* for Cohort 1 (e).

Figure 9:
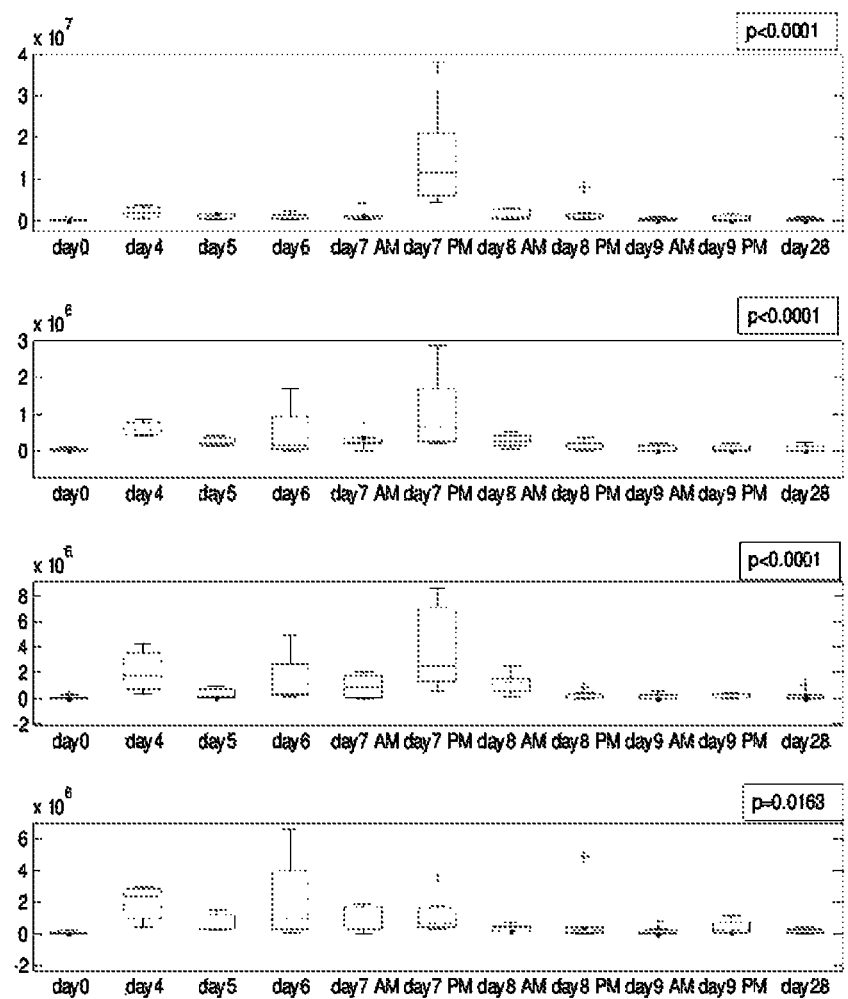

FIG. 9—Box plots Cohort 1 for each compound across the different days of breath collection, calculated using the area under the peak. Box plots correspond to (from top to bottom): (Z)-1-Methylthio-1-propene, (E)-1-Methylthio-1-propene, 1-Methylthio propane and allyl methyl sulfide. On each box, the central mark is the median, the edges of the box are the 25th and 75th percentiles, the whiskers extend to the most extreme data points not considered outliers, and outliers are plotted individually. The p-value shown on top of each box plot corresponds to the ANOVA test and it rejects the null hypothesis that all samples (from different collection days) are drawn from populations with the same mean.

Figure 10:
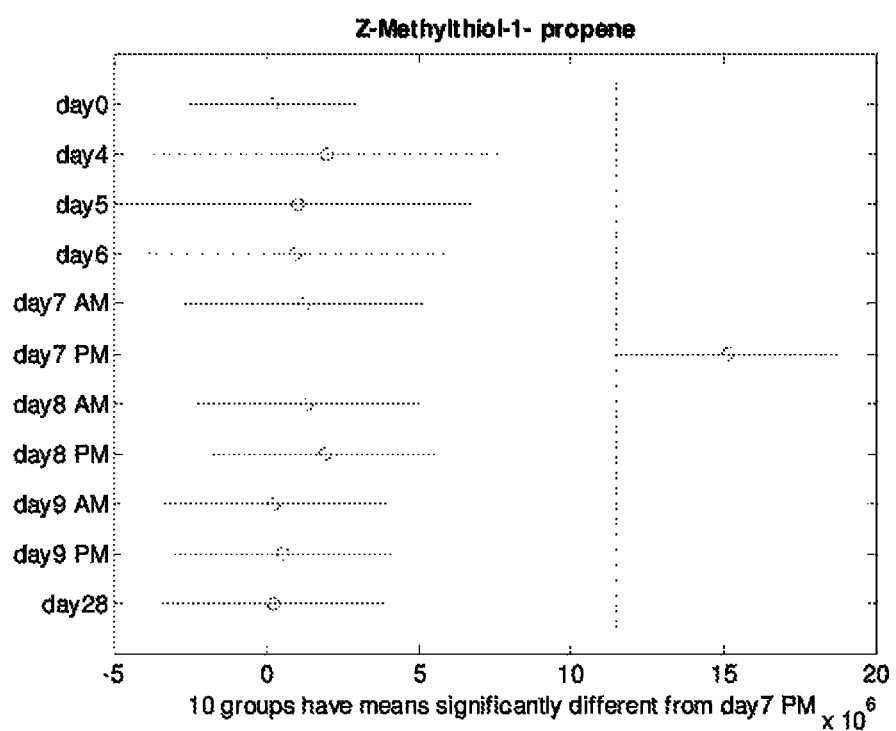

FIG. 10—Multicomparison test for (Z)-1-Methylthio-1-propene Cohort 1 showed that at day 7-pm, 6.5 hours after drug treatment, there were significant higher levels of the compound (no overlapping intervals).

FIG. 11—PCA score plot Cohort 1 based on GC-MS data (area under the peak) for four thioethers (allyl methyl sulphide, 1-methylthiopropane, (E)-1-methylthio-1-propene, and (Z)-1-methylthio-1-propene) and breath samples collected at baseline Day 0 (BL) (a), during malaria infection Day 7-AM (If) (b), after anti-malaria administration Day 7-PM (Drug) (c), at recovery phase Day 28 (Rec) (d), and an overlay of PCA score plots FIG. 11a to 11d for Cohort 2 (e).

Figure 12:
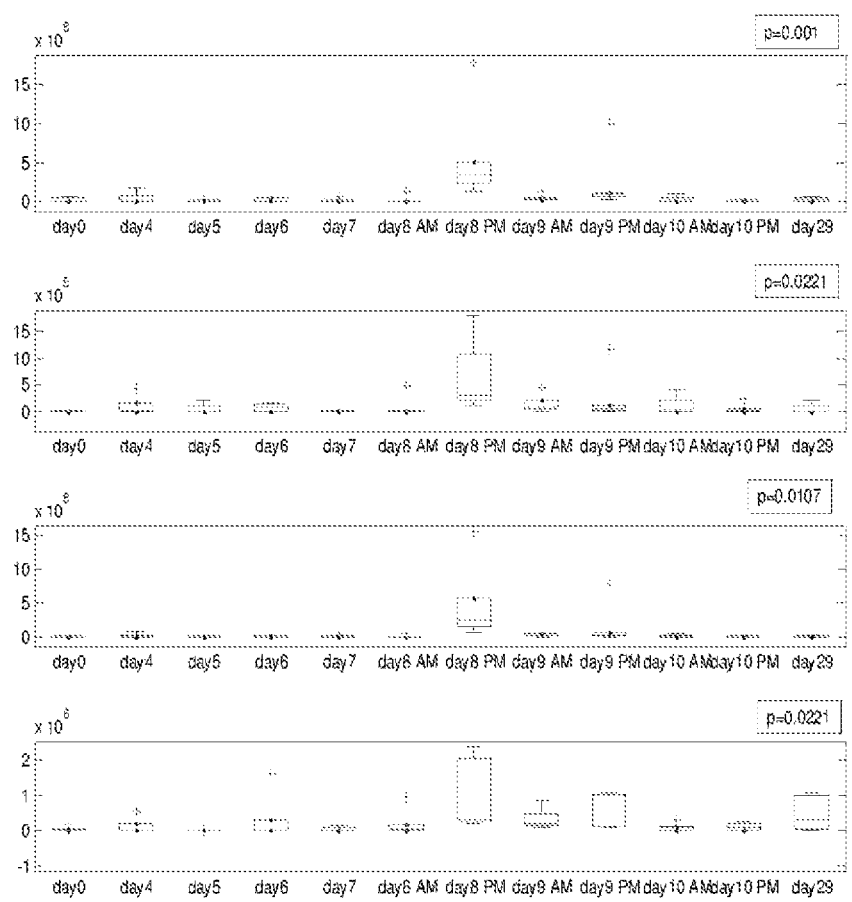

FIG. 12—Box plots Cohort 2 corresponds to (from top to bottom): (Z)-1-Methylthio-1-propene, (E)-1-Methylthio-1-propene, 1-Methylthio propane and allyl methyl sulfide. On each box, the central mark is the median, the edges of the box are the 25th and 75th percentiles, the whiskers extend to the most extreme data points not considered outliers, and outliers are plotted individually. The p-value shown on top of each box plot corresponds to the ANOVA test and it rejects the null hypothesis that all samples (from different collection days) are drawn from populations with the same mean.

Figure 13:
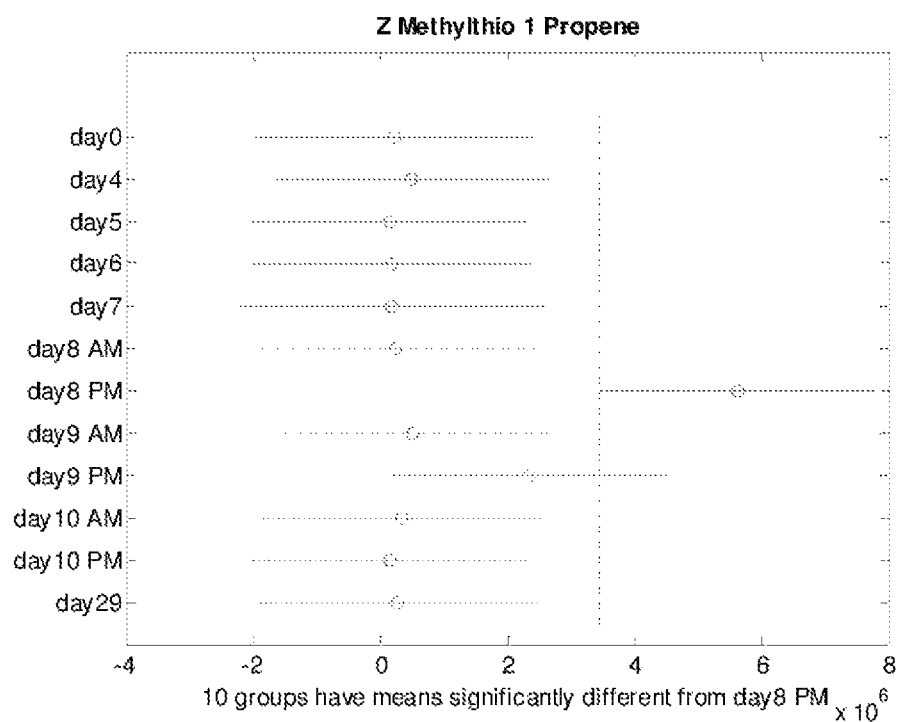

FIG. 13—Multicomparison test for (Z)-1-Methylthio-1-propene Cohort 2 showed that at day 8-pm, 6.5 hours after drug treatment, there were significant higher levels of the compound (no overlapping intervals).

Figure 14:
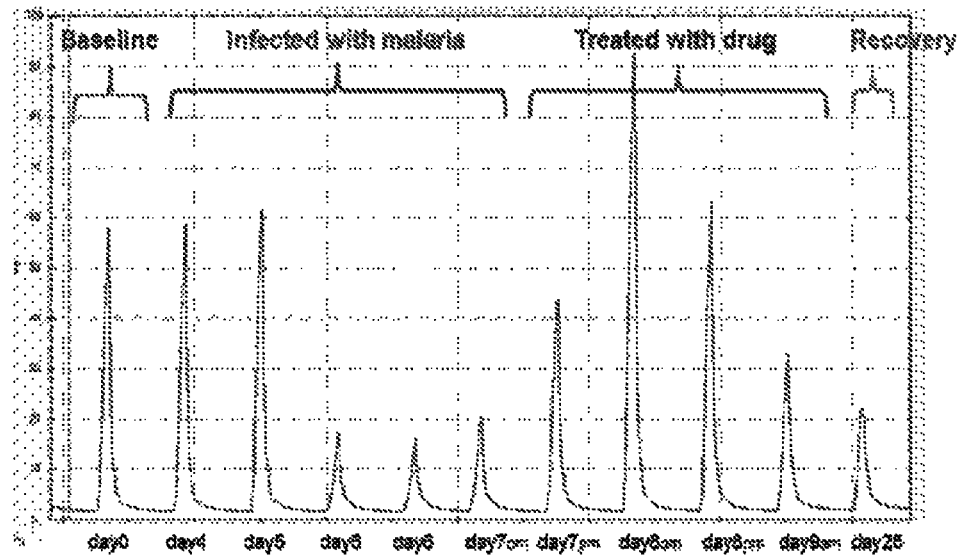

FIG. 14—Diagnose Enose responses to breath samples collected at different stages of the malaria study.

Figure 15:
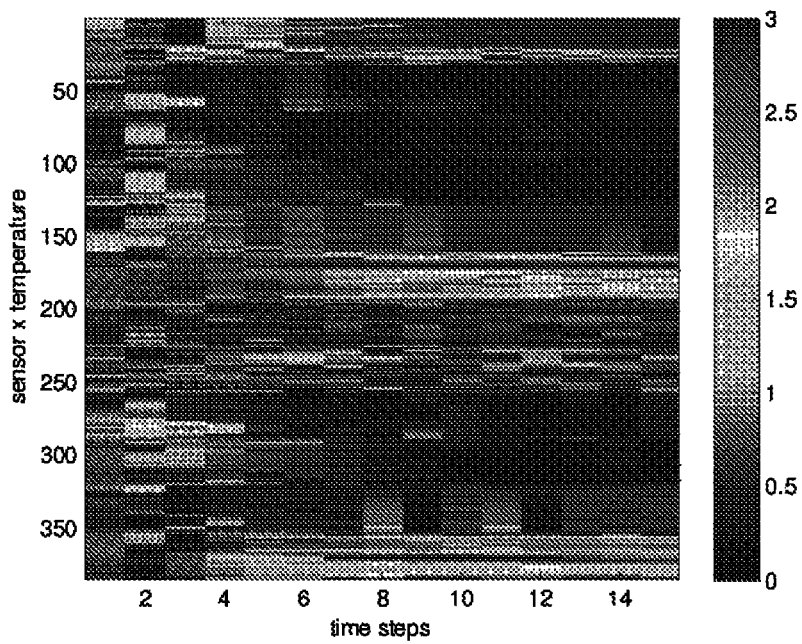

FIG. 15—Average pairwise distances of the mean class vectors for the two classes, control breath samples and spiked breath samples with allyl methyl sulfide (10 ppb). Each slice represents a feature of the Diagnose Enose and shows the differences between the two samples for each virtual sensor.

Figure 16:
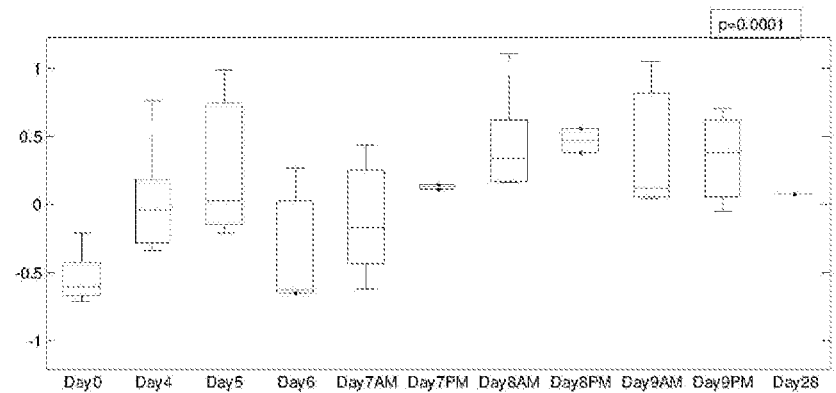

FIG. 16—Box plot using Diagnose Enose sensor number 2314 which corresponds to sensor 1 ($SnO_2$ doped with Ag) at time step 6 and thermal loop 1.0.

Figure 17:
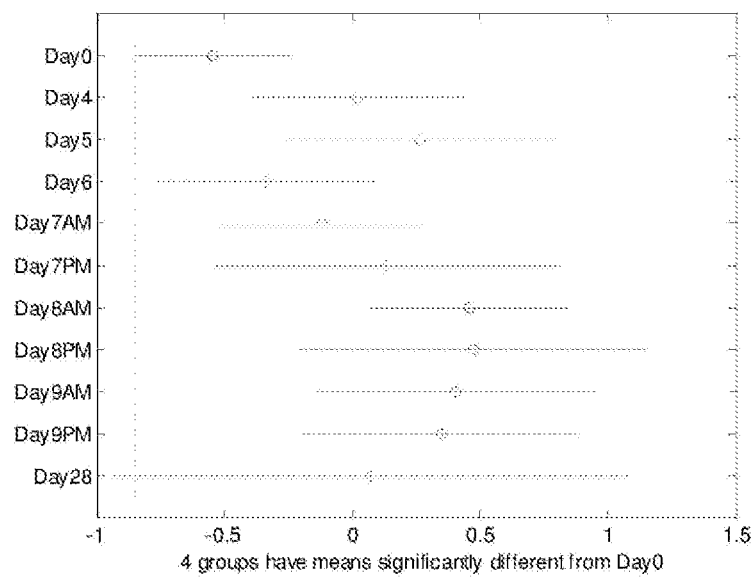

FIG. 17—Multicomparison test using Diagnose Enose sensor number 2314 which corresponds to sensor 1 ($SnO_2$ doped with Ag) at time step 6 and thermal loop 10.

Figure 18A:
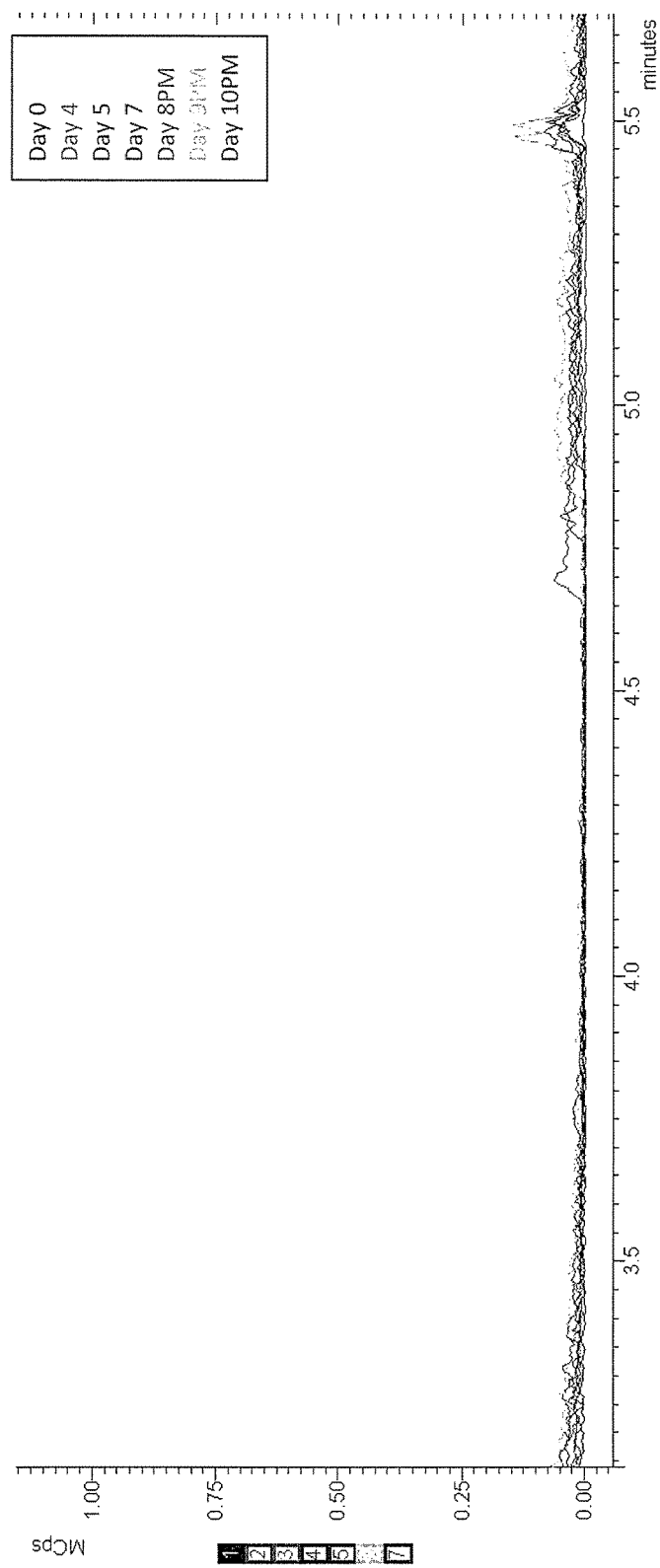

FIG. 18—(a) Single ion (m/z 88) GCMS chromatograms for different ambient air samples collected in Cohort 2 in the regions of thioethers: allyl methyl sulphide, (E)-1-methylthio-1-propene, and (Z)-1-methylthio-1-propene). No peaks can be observed indicating the absence (or not at detectable levels) of them in ambient air samples. (b) Single ion (m/z 90) GCMS chromatograms for different ambient air samples in the region of 1-methylthio-1-propene.

Figure 19:
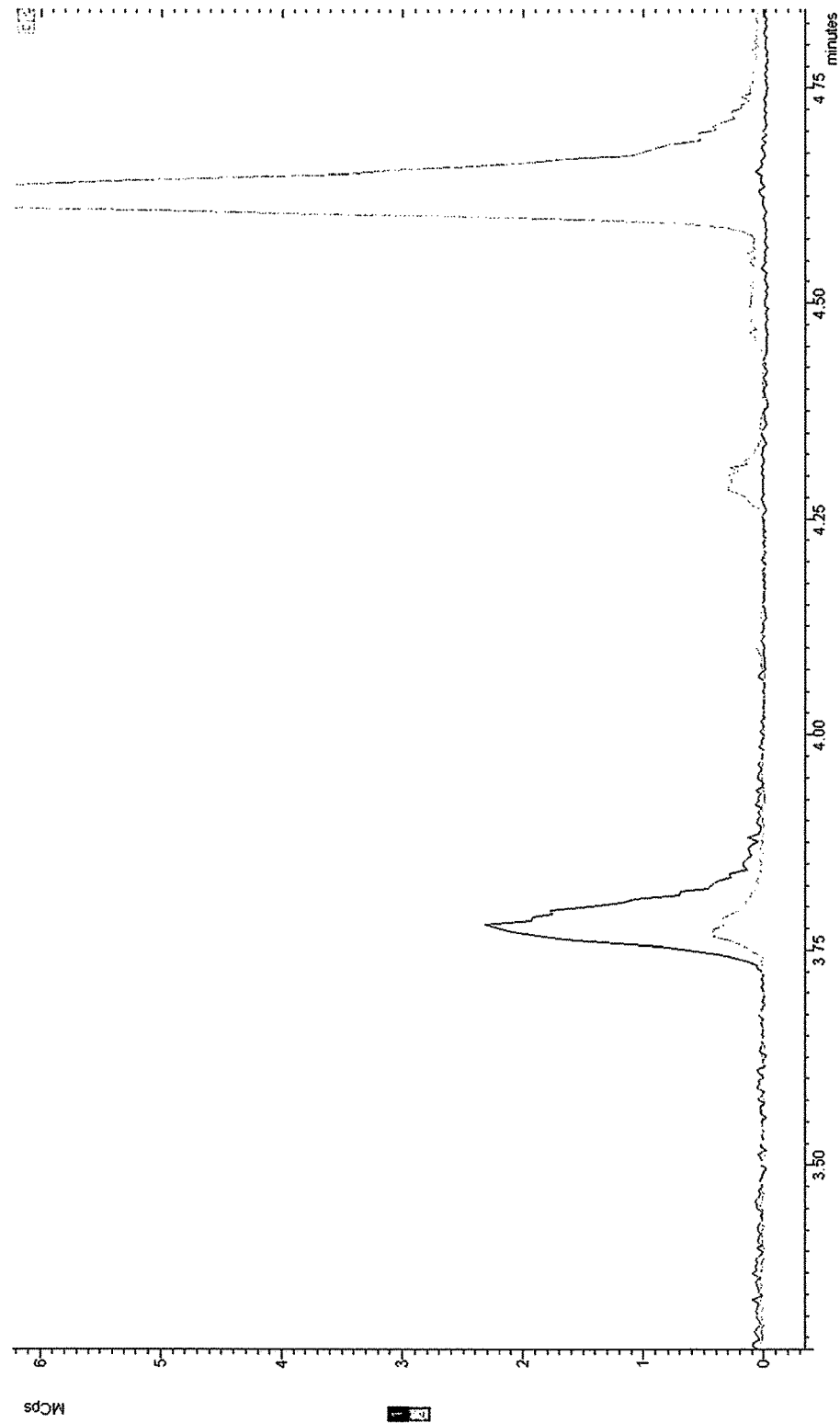

FIG. 19—Single ion (m/z 88) chromatograms showing the first five minutes of analysis time. Overlay of chromatogram from breath sample collected 6.5 hours after anti-malaria injection and breath spiked with allyl methyl sulfide (10 ppb) (allyl methyl sulfide ~RT 3.75*).

Figure 20:
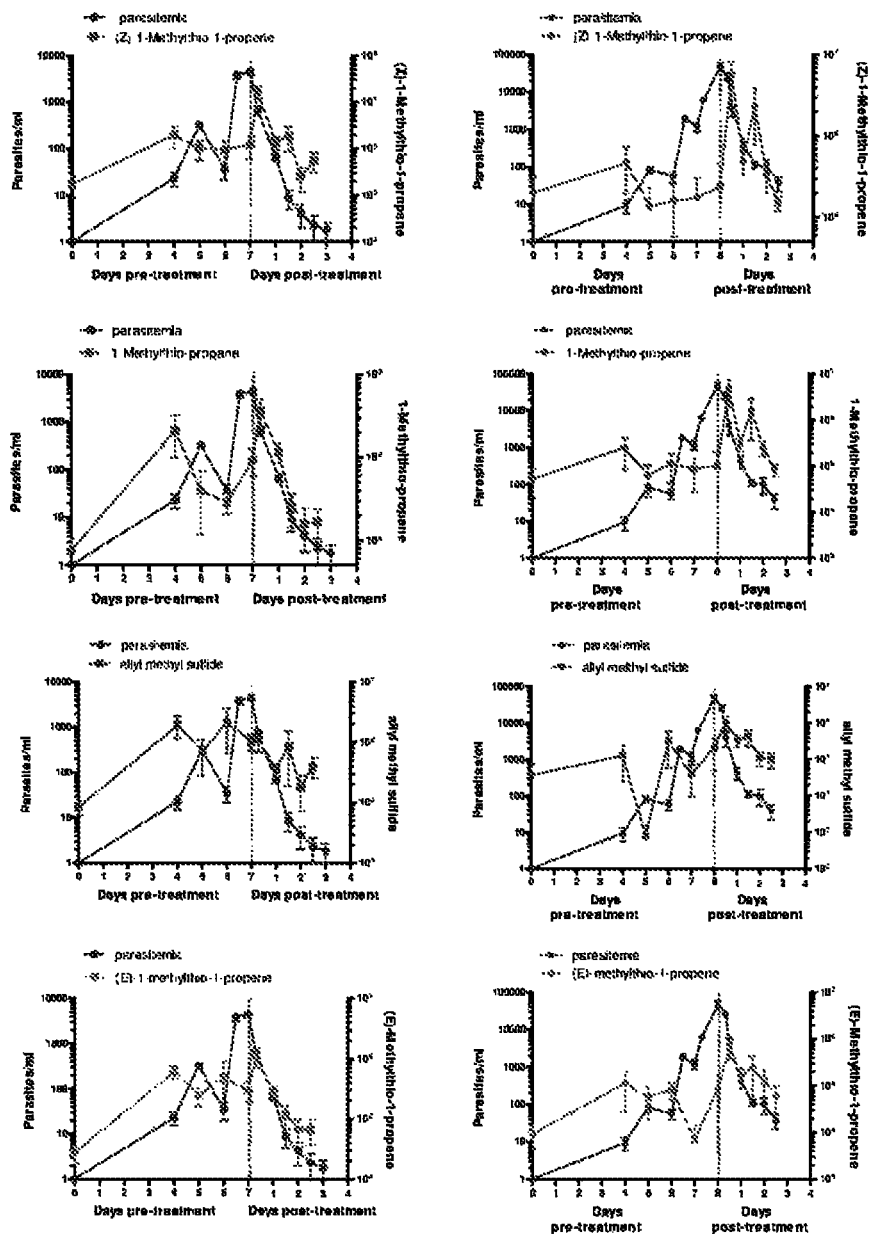

FIG. 20—Volatiles in breath vs parasite levels in blood for two cohorts over the course of malaria. Each participant in the cohort was inoculated on Day 0 with ~1,800 viable *Plasmodium falciparum*-infected human erythrocytes administered intravenously. Breath and blood samples were collected over the course of malaria. Drug treatment started on Day 7 for Cohort 1 (n=7, left panel) and on Day 8 for Cohort 2 (n=6, right panel) indicated by dotted vertical lines in the plots. Growth and clearance of parasitaemia are denoted by blue circles and abundance of compounds are denoted by squares: allyl methyl sulfide (m/z 88), (E)-1-methylthio-1-propene (m/z 88), (Z)-1-methylthio-1-propene (m/z 88) and 1-methylthio-propane (m/z 90).

Figure 21:
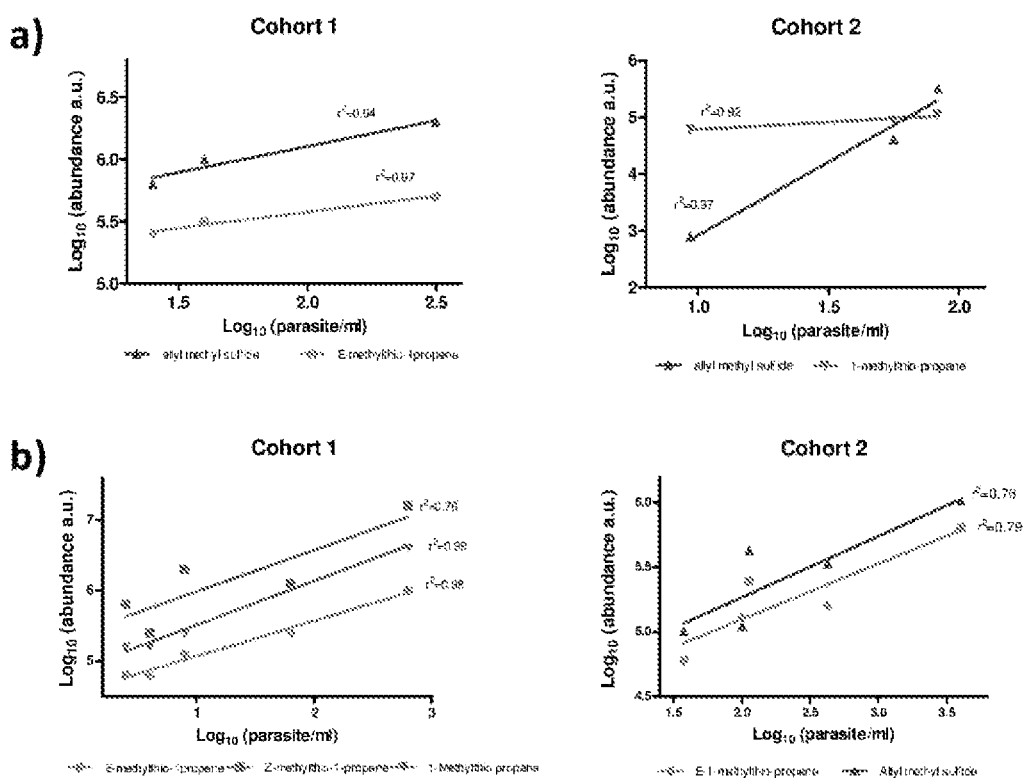

FIG. 21—Correlation of parasites level and abundance of malaria volatiles a) before and b) after treatment for the two cohorts. In Cohort 1, a fast acting synthetic ozonide drug was used on Day 7 and in Cohort 2 piperaquine was administered on Day 8.

Figure 22:
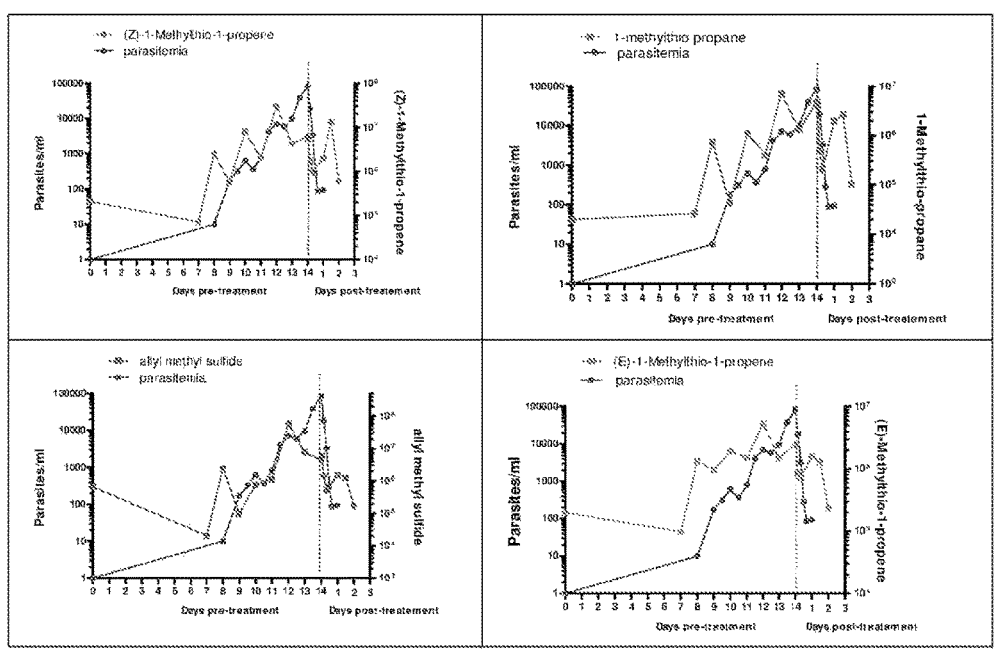

FIG. 22—Growth and clearance of parasitemia in RBC and breath abundance of allyl methyl sulfide (m/z 88), (E)-1-methylthio-1-propene (m/z 88), (Z)-1-methylthio-1-propene (m/z 88) and 1-methylthio-propane (m/z 90) in a human volunteer over the course of malaria *P. vivax* infection.

DETAILED DESCRIPTION OF THE INVENTION

General Techniques and Selected Definitions

Unless specifically defined otherwise, all technical and scientific terms used herein shall be taken to have the same meaning as commonly understood by one of ordinary skill in the art (e.g., in cell culture, parasitology, malaria detection, molecular genetics, volatile compound detection methods, immunology, immunohistochemistry, protein chemistry, and biochemistry).

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "identifying a subject with a *Plasmodium* infection" also refers to diagnosing the infection. For instance, the method can be used to distinguish malaria fever from non-malarial fever as symptoms of malaria can be similar to those of many different infectious diseases or other illnesses, including viral illnesses, such as a cold or flu, diseases from tick bites (*rickettsia*), stomach infections (gastroenteritis), inflammation of the liver (hepatitis), severe fever caused by bacteria (typhoid fever), bacterial infection or inflammation of the brain or spinal cord (bacterial meningitis), other infections caused by parasites.

As used herein, the term "monitoring a subject with a *Plasmodium* infection" refers to observations of the infection over time, such as hours, days, weeks or months. As outlined herein, the subject can be monitored following being administered with a compound in an attempt to treat the disease.

As used herein, the term "indicative of the status" refers to the level of disease burden on the subject. This is particularly relevant if the subject is undergoing treatment for a *Plasmodium* infection, or when deciding a suitable treatment for the infection. As described herein, an initial increase in the levels of the VOC(s) suggests that the treatment is working, whereas the levels reaching similar to those seen in healthy subjects suggesting the treatment has been effective or possibly cured of all *Plasmodium* sp. Furthermore, the present inventors have found that, apart from short-term fluctuations following initial treatment, the levels of the defined VOCs, in particular allyl methyl sulphide, are indicative of the total number of *Plasmodium* in the subject. Thus, the term "indicative of the status" also refers to the total number of *Plasmodium* (parasites) in the subject.

The term "volatile organic compounds", which may also be abbreviated to "VOCs", refers to organic chemicals that have a high vapor pressure at ordinary, room-temperature conditions. Accordingly, it will be understood that a single "volatile organic compound" may be abbreviated to VOC. The high vapor pressure of the VOCs results from a low boiling point, which causes large numbers of molecules to evaporate or sublimate from the liquid or solid form of the compound into the gaseous state.

As understood in the art the use of "E" and "C" in reference to 1-methylthio-1-propene is the notation used to describe the geometric isomerism, or stereochemistry, of the double bond in 1-methylthio-1-propene.

As understood in the art the use of the terms "sulfur" and "sulfide" may also be referred to as "sulphur" and "sulphide" respectively.

As used herein, the term "following step i) an initial increase in the levels of the one or more volatile organic compounds, and/or a reduction in the levels of the one or more volatile organic compounds, indicates that the compound could be used to treat a *Plasmodium* infection" means that depending on when the subject or sample are analysed following treatment with the candidate compound a higher or lower level of the one or more VOCs (compared to the levels before administration of the compound) may be observed if the compound is having an anti-malarial effect. As described herein, an initial increase is generally observed shortly after administration of an effective treatment (especially for fast acting drugs) followed in a reduction to a lower amount than before the compound was administered. If the subject is monitored regularly both the increase, followed by the decrease (reduction), may be observed. However, it is possible to, for example, monitor at a single time point (for instance 30 days from the compound being administered) to determine if the treatment has had any effect.

As used herein, the term "lack of a significant change in the levels of the one or more volatile organic compounds" means that the levels of the one or more volatile organic compounds does not vary to a sufficient extent to suggest that a treatment has been effective, or that even if an initial increase is observed the levels of the one or more volatile organic compounds return to about the same as that before the treatment. For instance, a lack of a significant change may be, for example, less than +/−20%, or less than +/−10%, of the levels after treatment when compared to before treatment.

As used herein the terms "treating", "treat" or "treatment" include administering a therapeutically effective amount of a compound to try to reduce the severity of or eliminate at least one symptom of a *Plasmodium* infection, such as malaria, in a subject such as, for example, prostration, impaired consciousness, respiratory distress (acidotic breathing), gastrointestinal complaints (nausea, vomiting, diarrhea), multiple convulsions, circulatory collapse, pulmonary oedema (radiological), abnormal bleeding, jaundice, neurologic complaints (dizziness, confusion, disorientation, coma), headache, back pain, myalgia, chills, coughing and/or haemoglobinuria. Such terms also encompass a reduction in the parasitic load and/or inhibition of replication and/or a reduction in transmission of the parasite in the subject being treated.

Sample

The sample may be any material obtained from the subject which is known, or determined to have, the one or more volatile organic compounds.

In one embodiment, the sample is gaseous. Alternatively, the sample can be volatile organic compounds collected from a solid or liquid sample, for example from a bodily source such as tissue or fluid from a body. The sample may include body fluid or solid matter from the subject. Examples of suitable samples from a subject include, but are not necessarily limited to, exhaled breath, condensate breath, saliva, blood, sweat, skin microbiota, skin volatile sample and urine. In an embodiment, the sample is exhaled breath. In another embodiment, the sample is exhaled breath wherein the alveolar air has been excluded.

One exemplary embodiment of sample collection is depicted in FIG. 1 where exhaled breath is collected from a subject suspected of *Plasmodium* infection. The exhaled breath volatiles may be transferred from a breath bag to a sorbent tube using an electric pump as shown in FIG. 2 or the breath bag may be used directly.

In certain embodiments, the one or more volatile organic compounds are detected in the gas phase. The sample itself may be in the gas phase, for example exhaled breath from an individual, or the gas may be mixed with or generated from a solid or liquid sample, such as a sample grown in culture or medium.

In other embodiments the one or more volatile organic compounds may be detected in the liquid or solid phase of the sample.

In one embodiment the one or more VOCs may be detected directly from a subject, for example the exhaled breath of a human suspected of having or known to have *Plasmodium* infection may be exhaled directly into a detection or diagnostic device.

In another embodiment, the sample, such as a skin swab or urine sample, could be placed in a container and the VOCs detected using a suitable sensor in the container such as on the inside of the lid of the container.

The sample can be analysed immediately for volatile organic compounds, or stored under suitable conditions for later analysis.

The sample may be pre-concentrated prior to detection of the one or more VOCs. The pre-concentration step includes a variety of different procedures known to the skilled person such as the use of sorbent tubes, solid-phase microextraction (SPME), or cryogenic concentration.

Sorbent tubes are typically composed of glass and contain various types of solid absorbent material (sorbents). Commonly used sorbents include activated charcoal, silica gel, and organic porous polymers such as Tenax and Amberlite XAD resins. Sorbent tubes can be attached to an electric pump. The pump calibrated with a flow rate in ml/min draws a predetermined volume of gaseous sample through the sorbent tube. VOCs are trapped onto the sorbent material during this transfer or sampling period.

SPME techniques are used to collect VOCs at low concentrations for analysis. SPME is a sample preparation technique used both in the laboratory and on-site. SPME involves the use of a fiber coated with an extracting phase, that can be a liquid (polymer) or a solid (sorbent), which extracts different kinds of analytes (including both volatile and non-volatile) from different kinds of media, which can be in liquid, solid or gas phase. The quantity of analyte extracted by the fibre is proportional to its concentration in the sample as long as equilibrium is reached or, in case of short time pre-equilibrium, with help of convection or agitation. After extraction, the SPME fiber is transferred to the injection port of separating instruments, such as a Gas Chromatograph, where desorption of the analyte takes place and analysis is carried out. The attraction of SPME is that the extraction is fast and simple and can be done usually without solvents, and detection limits can reach parts per trillion (ppt) levels for certain compounds. SPME also has great potential for field applications; on-site sampling can be done even by nonscientists without the need to have gas chromatography-mass spectrometry equipment at each location.

Cryogenic concentration is a process that allows recovery of VOCs for reuse. The condensation process requires very low temperatures so that VOCs can be condensed. Currently, liquid nitrogen is used in the cryogenic (less than −160° C. condensation process.

Volatile Organic Compounds and *Plasmodium* Infection

As the skilled person would understand, biological systems are highly variable with many factors such as age, sex, genetic factors, general health, level of infection, stage of infection, infection history, and the like all potentially influencing the levels of a biomarker in an individual. Similarly, the species of *Plasmodium* may also be relevant because it is known that *Plasmodium vivax* and *Plasmodium ovale* are slower in their blood stage cycle than *Plasmodium falciparum* so *Plasmodium vivax* and *Plasmodium ovale* may take a different time to the release of the volatile organic compounds.

Furthermore, the timing of malaria infection until symptoms appear (incubation period) generally ranges from:

9 to 14 days for *P. falciparum*,
12 to 18 days for *P. vivax* and *P. ovale*,
18 to 40 days for *P. malariae*, and
11 to 12 days for *P. knowlesi*.

Furthermore, the paroxysms or cyclical fevers classically associated with malaria occur shortly before or at the time of erythrocyte rupture. Infection with *P. malariae* causes paroxysms every 72 hours (quartan malaria). Infection with *P. ovale* or *P. vivax* cause tertian malaria with paroxysms every 48 hours. *P. falciparum* tends to produce irregular fever spikes superimposed upon a continuous fever or the tertian malaria paroxysms every 48 hours. Thus, depending on the stage of infection the levels of the VOCs may vary. In particular, if it is possible the subject has only recently become infected, it may be necessary to repeat the method, for example in 9 to 40 days' time, to double check a negative result.

The present inventors have shown a clear correlation between *Plasmodium* infection and the levels of the volatile organic compounds allyl methyl sulphide, 1-methylthiopropane, (E)-1-methylthio-1-propene, and (Z)-1-methylthio-1-propene.

The present inventors have shown that the level of allyl methyl sulphide has the strongest correlation with the detection of the presence of a *Plasmodium* infection.

The methods of the invention can be performed in a variety of ways. For instance, a defined level can be used as an indicator for *Plasmodium* infection, such as greater than 15 parts per trillion (ppt) of allyl methyl sulfide in an exhaled breath sample. In another embodiment, the level of the VOC(s) in a test subject can be compared to that in the same type of sample from a control subject(s) known not to have a *Plasmodium* infection, with higher levels (for example at least two-fold higher levels) in the sample from the test subject indicative of a *Plasmodium* infection. In an embodiment, the data from one or more control samples may be stored as a reference collection of data.

The present inventors have also shown that the levels of these VOCs typically increase after the subject is treated for the *Plasmodium* infection before returning to levels, or close thereto, of a subject without a *Plasmodium* infection. The timing of the initial increase will not only vary to some degree because of the factors mentioned above, but also because of the treatment. For instance, slow acting treatments are likely to mean the "initial" increase occurs later following the treatment than if a faster acting treatment is used. As the skilled person would understand, regular monitoring of the patient will ensure the "initial increase" is detected. In an embodiment, the initial increase occurs between about 0.5 hours and about 7 days, or between about 0.5 hours and about 5 days, or between about 0.5 hours and about 3 days, or between about 0.5 hours and about 24 hours, or between about 0.5 hours and about 12 hours, or between about 0.5 hours and about 8 hours, after being administered with the treatment.

Furthermore, the present inventors have shown that the level of (Z)-1-methylthio-1-propene has the strongest correlation with the initial increase following administration with a compound to treat the infection. Thus, of the VOCs correlated with *Plasmodium* infection described herein (Z)-1-methylthio-1-propene is the best marker for treatment efficacy (i.e., the ability of the treatment to kill the parasite).

In an embodiment, the initial increase is observed when using fast acting treatments. Examples of fast acting antimalarial drugs include chloroquine, quinine, mefloquine, atovaquone and artemisinin, whereas examples of slow acting antimalarial drugs include proguanil, pyrimethamine, sulfamides and tetracyclines. Fast acting drugs can be identified using the methods described in Le Manach et al. (2013), such as having an IC50 speed assay of less than 1.5.

In addition, the present inventors have shown that the level of (E)-1-methylthio-1-propene has the strongest correlation with effective treatment of the infection, and hence is the best marker for determining the kinetics of parasite clearance following treatment (i.e. reduction or total absence of parasite load following conclusion of treatment).

In another embodiment, the levels of one or more volatile organic compounds may be indicative of the life cycle stage of the parasite and the parasitic load. For instance, the current data suggests that thioether levels may be linked to a specific phase in the ring, trophozoite, schizont and merozoite cycle. Although the inventors sampling regime did not have the resolution to precisely define the association, the 180° phase-shift from maximum parasitaemia and the peak of thioethers that occurs shortly after drug treatment suggests that the bursting of erythrocytes (schizont rupture) to release merozoites and infect new red blood cells may be the event that triggers maximal thioether release.

Based on the experimental data provided herein, the skilled person can readily perform routine experiments to determine the levels the VOCs, or combinations of one or more thereof, which are indicative of a *Plasmodium* infection. In one embodiment, the detection of, for example in an exhaled breath sample, greater than 15 parts per trillion (ppt) of allyl methyl sulfide is indicative of *Plasmodium* infection. In another example, a level of at least 300 ppt allyl methyl sulphide, for example in an exhaled breath sample, indicates the treatment is being effective.

In an embodiment, especially when monitoring a subject with a *Plasmodium* infection or identifying a compound to treat a *Plasmodium* infection, the method may compare the fold change in the one or more VOCs. For instance, when identifying a compound to treat a *Plasmodium* infection the fold changes in the VOCs between one of more of i) the subject or sample therefrom before infection, ii) the subject or sample therefrom following infection and before drug administration, iii) at various stages (time) following administering a candidate compound, can be determined and compared.

Since the levels of the one or more volatile organic compounds can be used to indicate the status of the *Plasmodium* infection this allows the determination of the levels to be used to select a suitable treatment for the infection. As the skilled person would be aware, 1) Uncomplicated malaria can be treated orally when parasitaemia is <1%, 2) Intravenous treatment is usually given when malaria is considered severe (www.cdc.gov/malaria/diagnosis_treatment/clinicians3.html). WHO criteria for severe malaria is >10,000 parasites/µl. Once the parasite density is <1% the patient can take oral medication, and 3) Exchange transfusion is considered when parasitaemia is 10% (Hanscheild, 1999).

In the induced blood stage malaria (IBSM) protocol used for the study described in the Examples, for ethical reasons, the maximum parasitaemia levels allowed was only 0.001%. Thus, precise levels of the VOCs and parasite load for selecting a suitable treatment have not yet been determined. Nonetheless, the inventors have shown a clear correlation between the levels of the VOCs and parasite load, and hence suitable data to enable the exact determination of which levels of the VOCs are associated with less than <1% parasitaemia (and hence oral treatment selected), between 1% and less than 10% parasitaemia (and hence intravenous treatment selected), and 10% or greater parasitaemia (and hence transfusion selected) can easily be determined using very simple and routine procedures in light of the present disclosure. An estimation for allyl methyl sulfide would be that a value of about 300 ppt will correspond to about 0.001% parasitaemia, and hence oral intervention would be recommended in such a case.

Detection

The one or more volatile organic compounds can be detected/monitored or similar by any technique known in the art. Examples include, but are not limited to, one or more of spectrometry, for example mass spectrometry (MS) (such as gas chromatography mass spectrometry (GCMS), liquid chromatography mass spectrometry (LCMS) and proton transfer reaction mass spectrometry (PTR-MS)), ion mobility spectrometry, field asymmetric ion mobility spectrometry, differential mobility spectrometry (DMS); electronic nose device; biosensor; an antibody-based detection system; colorimetric assays; infrared spectroscopy (IR spectroscopy) (such as near-infrared (NIR), selected ion flow tube mass spectrometry (SIFT). Fourier Transform-Infrared (FTIR) spectroscopy and ring-down cavity spectroscopy); fuel cell electrodes; light absorption spectroscopy; nanoparticle technology; flexural plate wave (FPW) sensors; electrochemical sensors; photoacoustic equipment; laser-based equipment; various ionization techniques and trained animal detection or combinations thereof. In one example, the one or more volatile organic compounds are detected/monitored or similar using gas chromatography mass spectrometry (GCMS), an electronic nose device or biosensor.

Mass spectrometry works by ionizing molecules, to generate charged molecules or molecule fragments, and measuring their mass-to-charge ratios. The mass spectrometry component of the detection techniques includes quadrupole, time of flight, tandem mass spectrometry, ion cyclotron resonance, and/or sector (magnetic and/or electrostatic).

Mass spectrometry can be used it in tandem with chromatographic separation techniques. For example, GCMS is an analytical method that combines the features of gas chromatography and mass spectrometry to identify compounds. Similarly, liquid chromatography mass spectrometry (LCMS) is an analytical method that combines the features of liquid chromatography and mass spectrometry to identify compounds. The chromatographic separation component of these techniques relies on the difference in chemical properties of different molecules in a mixture and allows the separation of the molecules as the sample travels through the column. Each molecule has a characteristic retention time in which it passes through the column under set conditions. This allows the mass spectrometer component of the technique to capture, ionize, accelerate, deflect and detect the ionized molecules, or molecular fragments, separately.

Proton transfer reaction mass spectrometry (PTR-MS) is a very sensitive technique for online monitoring of volatile organic compounds (VOCs). A PTR-MS instrument consists of an ion source that is directly connected to a drift tube and a mass spectrometer.

Ion-mobility spectrometry (IMS) is an analytical technique used to separate and identify ionized molecules in the gas phase based on their mobility in a carrier buffer gas. This technique can be coupled with mass spectrometry and/or chromatographic separation techniques. For example, ion mobility spectrometry-mass spectrometry (IMS-MS) is a technique where ions are first separated by drift time through some neutral gas under an applied electrical potential gradient before being introduced into a mass spectrometer. Drift time is a measure of the radius relative to the charge of the ion. The duty cycle of IMS is longer than most mass spectrometric techniques, such that the mass spectrometer can sample along the course of the IMS separation. This produces data about the IMS separation and the mass-to-charge ratio of the ions in a manner similar to LC/MS. The duty cycle of IMS is short relative to liquid chromatography or gas chromatography separations and can thus be coupled to such techniques, producing triple modalities such as LC/IMS/MS.

Differential mobility spectrometry ions are distinguished by the difference between mobilities at high and low electric fields due to the fact that ion mobility values depend on the applied field strength. The method is easy to use, sensitive, fast and relatively selective.

FTIR is a technique which is used to obtain an infrared spectrum of absorption, emission, photoconductivity or Raman scattering of a solid, liquid or gas. The goal of any absorption spectroscopy is to measure how well a sample absorbs light at each wavelength. One way to do this is to shine a monochromatic light beam at a sample, measure how much of the light is absorbed, and repeat for each different wavelength. Fourier transform spectroscopy is a less intuitive way to obtain the same information. Rather than shining a monochromatic beam of light at the sample, this technique shines a beam containing many frequencies of light at once, and measures how much of that beam is absorbed by the sample. Next, the beam is modified to contain a different combination of frequencies, giving a second data point. This process is repeated many times. Afterwards, a computer takes all these data and works backwards to infer what the absorption is at each wavelength.

Selected ion flow tube mass spectrometry (SIFT-MS) is a quantitative mass spectrometry technique for trace gas analysis which involves the chemical ionization of trace volatile compounds by selected positive precursor ions during a well-defined time period along a flow tube.

Ring-down cavity spectroscopy is another variant of infrared spectroscopy that is particularly sensitive to trace-levels of gas and may be especially suitable for diagnosis of malaria in breath using the claimed compounds.

An electronic nose (also referred to as E-nose) is a device that detects odors. This technique may also be referred to as "electronic sensing" or "e-sensing". Electronic noses include three major parts: a sample delivery system, a detection system, a computing system. The sample delivery system enables the generation of the headspace (volatile compounds) of a sample, which is the fraction analyzed. The system then injects this headspace into the detection system of the electronic nose. The detection system, which consists of a sensor set, is the "reactive" part of the instrument. When in contact with volatile compounds, the sensors react, which means they experience a change of electrical properties. In most electronic noses, each sensor is sensitive to all volatile molecules but each in their specific way. However, in bio-electronic noses, proteins which respond to specific odor molecules are used. Most electronic noses use sensor arrays that react to volatile organic compounds on contact and/or the adsorption of volatile organic compounds on the sensor surface causes a physical change of the sensor. A specific response is recorded by the electronic interface transforming the signal into a digital value. Recorded data are then computed based on statistical models.

The sensors for electronic noses include metal-oxide-semiconductors (MOSFET), metal oxide sensors (MOX), conducting polymers, polymer composites, quartz crystal microbalance, surface acoustic wave (SAW).

In metal-oxide-semiconductor (MOSFET) devices a transistor is used for amplifying or switching electronic signals. This works on the principle that molecules entering the sensor area are charged either positively or negatively, producing a change in the MOSFET signal that can then be interpreted by pattern recognition computer systems. Therefore, each detectable molecule has its own unique signal.

Metal oxide semiconductor (MOX) sensors use metal oxide-based sensing thick films deposited onto a Si-micromachined substrate (micro sensors). The substrate contains electrodes that measure the resistance of the sensing layer, and a heater that heats the sensing layer to 200° C. to 400° C. The sensor responds to changes in the composition of the ambient atmosphere with a change in the resistance of the sensing layer.

Conducting polymers are organic polymers that conduct electricity. Polymer composites are similar in use to conducting polymers but formulated of non-conducting polymers with the addition of conducting material such as carbon black.

Quartz crystal microbalance is a way of measuring mass per unit area by measuring the change in frequency of a quartz crystal resonator. This can be stored in a database and used for future reference.

Surface acoustic wave (SAW) is a class of microelectro-mechanical systems (MEMS) which rely on the modulation of surface acoustic waves to sense a physical phenomenon.

Nanoparticle sensors have unique physical, chemical and biological properties and functional activity. The nanoparticle size and shape are connected with surface area and quantum effects. Reducing the size of the nanoparticles leads to the fact that, compared with internal content, a significantly greater proportion of atoms (the components of the nanoparticles) is on the surface.

Biosensors have a biological component with a physico-chemical detector. Accordingly, an electronic nose with a biological component is a type of biosensor. A biosensor typically consists of a bio-recognition component, biotransducer component, and electronic system which include a signal amplifier, processor, and display.

The biological component may be, for example, cells or proteins. Examples of suitable proteins include, but are not limited to, an antibody or fragment thereof which binds a VOC defined herein, or a receptor, such as G coupled protein receptor (GPCR) (for example odorant or taste GPCRs), which binds a VOC defined herein. In an embodiment, the protein is labelled with a detectable label. For example, the G coupled protein receptor can be labelled with a RET pair such that the spatial location and/or dipole orientation of the RET donor molecule (such as a bioluminescent protein) relative to the RET acceptor molecule is altered when the VOC binds the GPCR (see, for example, WO 2004/057333 and WO 2010/085844). In an alternate embodiment, the protein is an antibody or fragment thereof and the binding of the antibody or fragment thereof is detected by the use of a labelled secondary agent (for example secondary antibody) as is known in the art.

An example of a biosensor which can be adapted for use in the methods of the invention is described in WO 2013/155553.

As the skilled person would appreciate, antibodies or fragments thereof which bind a VOC defined herein can also be used in a wide variety of different standard detection systems such as an enzyme-linked immunosorbent assay (ELISA) or immunohistochemical staining.

In an embodiment, a method is performed using microfluidics such as described in WO 2013/155553.

In an embodiment, the biosensor may involve a chelated metal ion as described in Australian Provisional Patent Application 2014904612.

In certain embodiments, a point-of-care diagnostic device is used to identify the one or more VOCs. Preferably, the point-of-care diagnostic tool is portable and may detect VOCs to low limits of detection.

Anti-*Plasmodium* Compounds

An anti-*Plasmodium* compound may also be referred to as an antimalarial compound or an antimalarial.

An anti-*Plasmodium* compound is a compound that is used to treat and/or prevent *Plasmodium* infection. The term "anti-*Plasmodium* compound" may also refer to a combination of compounds (i.e. a combination therapy) that are used to treat and/or prevent *Plasmodium* infection.

Examples of anti-*Plasmodium* compounds include, but are not limited to, artemether-lumefantrine, artemether, amodiaquine, artemisinin, artesunate, clindamycline, chloroquine, doxycycline, dihydroartemisinin, mefloquine, naphroquine, proguanil, piperaquine, primaquine, pyronaridine, quinine, sulphadoxine-pyrimethamine, tetracycline, OZ439, and combinations thereof. As described herein, a subject with a *Plasmodium* infection can be administered with anti-*Plasmodium* such as those mentioned above and monitored using a method of the invention to determine the success of the treatment.

A lack of treatment success, for instance determined by the levels of one or more or all of the VOCs being similar (for example +/−20% or +/−10%) before and after treatment, may indicate that the subject is infected with a *Plasmodium* strain resistant to the treatment (and hence an alternate treatment should be applied), or the active component of the treatment used had been compromised (past expiry date and/or not stored correctly), or not present at a sufficient concentration or completely lacking (anti-malarial drug counterfeiting is a serious problem—see Karunamoorthi, 2014).

As described herein, the levels of VOCs can be used to decide the most appropriate treatment for the infected subject.

In the context of screening for new anti-malarial compounds, by a "candidate compound" is meant an agent to be evaluated for treating or preventing a *Plasmodium* infection, such as treating malaria. A candidate compound (may also be referred to as a drug candidate) includes a compound that is going through the drug discovery process. Candidate compounds may include, for example, small molecules, peptides or mimetics thereof, polypeptides, antibodies, nucleic acid molecules such as aptamers, peptide nucleic acid molecules, and components, combinations, and derivatives thereof.

Candidate compounds can be assessed in human and non-humans. The non-humans, such as mice or rats, may be transgenic.

McCarthy et al. (2011) describe a study for assessing the efficacy of new drug candidates for the treatment of *P. falciparum* infection. The study demonstrated safety in the 19 volunteers tested, and a significant difference in the clearance kinetics of parasitemia between the drugs in the 13 evaluable volunteers, with mean parasite reduction ratios of 759 for artemether-lumefantrine (A/L) and 17 for atovaquone-proguanil (A/P) (95% CI 120-4786 and 7-40 respectively; p, 0.01). The methods of the invention can be used with, for example, those described by McCarthy et al. to identify new anti-*Plasmodium* compounds.

Humanized mice have been developed for identifying new anti-malaria compounds (see, for example, Vaughan et al., 2012). The methods of the invention can be used with, for example, those described by Vaughan et al. (2012), to identify new anti-*Plasmodium* compounds.

Screening

The present invention can be used to screen for a compound for identifying a subject with a *Plasmodium* infection. Such compounds may bind or react with a VOC defined herein. Thus, in the context of screening for a compound for identifying a subject with a *Plasmodium* infection, by a "candidate compound" is meant an agent to be evaluated for use in methods of identifying or monitoring a *Plasmodium* infection. Candidate compounds may include, for example, small molecules, peptides or mimetics thereof, polypeptides, antibodies, nucleic acid molecules such as aptamers, peptide nucleic acid molecules, and components and derivatives thereof. In one embodiment, the candidate compound is a solid state sensor composition. For example, the solid state sensor composition may be a doped and undoped metal oxide sensor. In one embodiment the solid state sensor composition is a metal oxide sensor selected from tin dioxide ($SnO_2$) and tungsten trioxide ($WO_3$), wherein the oxide sensor is optionally doped with a metal selected from the group consisting of palladium (Pd), platinum (Pt), silver (Ag), copper (Cu), or combinations thereof (such as platinum silver compounds (PtAg)). In one embodiment, the sensor composition is tin dioxide doped with silver ($SnO_2$ doped with Ag).

As the skilled person would appreciate there are a wide variety of different screening procedures which could be adapted to screen for compounds which bind or react with a VOC defined herein. Examples include, but are not limited to, receptor protein (such as GPCR) library screening, surface plasmon resonance, high-resolution NMR, phage display, affinity chromatography, isothermal titration calorimetry (ITC), immunoprecipitation and GST pull downs coupled with mass spectroscopy.

In one embodiment, high throughput screening methods are used which involve providing a library containing a large number of candidate compounds. Such libraries are then screened in one or more assays to identify those library members (particular chemical species or subclasses) that display a desired characteristic binding or activity.

High throughput screening systems are commercially available and typically automate entire procedures, including all sample and reagent pipetting, liquid dispensing, timed incubations, and final readings of the microplate in detectors appropriate for the assay. These configurable systems provide high throughput and rapid start up as well as a high degree of flexibility and customization. The manufacturers of such systems provide detailed protocols for various high throughput systems.

Surface Plasmon Resonance (SPR) or Biomolecular Interaction Analysis (BIA; e.g., Biacore) detects biospecific interactions in real time, without labeling any of the interactants. Changes in the mass at the binding surface (indicative of a binding event) of the BIA chip result in alterations of the refractive index of light near the surface. The changes in the refractivity generate a detectable signal, which are measured as an indication of real-time reactions between biological molecules.

In one embodiment, the screening method comprises contacting one or more of allyl methyl sulphide, J-methylthiopropane, (E)-1-methylthio-1-propene, and (Z)-1-methylthio-1-propene, with a library of GPCRs (for example taste or odorant, or a combination thereof, GPCRs from nematodes or insects) expressed in cells (such as yeast cells), and identifying specific receptors which bind one of the VOCs. Such yeast cells will typically comprise a genetically engineered reporter system to detect receptor binding (see, for example, Fukutani et al., 2012; and Dowell and Brown, 1999).

EXAMPLES

Example 1—Materials and Methods

Controlled Human Malaria Infection

The study was approved by the Queensland Institute of Medical Research Human Research Ethics Committee (QIMR-HREC), and endorsed by the CSIRO Animal, Food and Health Sciences Human Research Ethics Committee (proposal number: 13/03).

This research was a controlled study using a blood stage *Plasmodium falciparum* (BSPC) inoculum challenge to characterize the efficacy of two anti-malaria drugs against early *Plasmodium falciparum* blood stage infection. Investigation of breath volatiles was an "add-on" to the anti-malarial efficacy studies. The study was conducted in two cohorts (n=8 for Cohort 1 and n=7 for Cohort 2) using different anti-malaria drugs. The anti-malaria drug investigated in Cohort 1 was OZ439 and the drug used in Cohort 2 was Piperaquine. OZ439, as an artemisin derivative, is rapidly absorbed, acts rapidly and is short-lived in the body. Piperaquine is absorbed slowly and has a long half-life in the body. Piperaquine was used widely as an antimalarial from the 60's to the 80's, but resistance developed and it fell out of favour. However, it is now being trialled as a combination therapy with artemisins, to balance their short-lived activity.

Each participant in the cohort was inoculated on Day 0 with ~1,800 viable *Plasmodium falciparum*-infected human erythrocytes administered intravenously. On an outpatient basis, participants were monitored daily (AM) or morning (AM) and evening (PM), from day 3 until PCR positive for presence of malaria parasites, for adverse events and the unexpected early onset of symptoms, signs or parasitological evidence of malaria.

On the day designated for commencement of treatment, as determined by qPCR results (usually Day7/8 AM), participants were admitted to the study unit and confined for safety monitoring and anti-malaria drug administration with parasite load and drug levels being monitored. The threshold for commencement of treatment was when PCR quantification was confirmed to be ≥1,000 parasites/mL. If clinical features or parasitological evidence of malaria occurred, or PCR quantification of ≥1,000 parasites/mL was detected before day 7 (AM) morning, allocated treatment began at this time (Tables 1 and 2).

Following treatment with anti-malaria, participants were followed up as inpatients for at least 48 hours, to ensure tolerance of the therapy and clinical response, then, if clinically well on an outpatient basis for safety and continued presence of malaria parasites via PCR. Compulsory commencement of treatment with Riamet® (active ingredients artemether and lumefantrine) started on day 24/25. Early intervention can occur if either poor responses or fast responses are seen following anti-malaria treatment. This was done to ensure patient safety. Table 3 summarises the events of the malaria study for Cohort 1 and 2.

TABLE 1

Dates of breath collection (as indicated by ticks) for Cohort 1 treatment with anti-malaria drug OZ439. Breath was collected at baseline (day 0 AM), after malaria infection and before administration of anti-malaria (day 0 PM-Day 7 AM), after administration of anti-malaria drug (day 7 PM-day 9 PM) and at the recovery phase (day 28 AM).

| | Day | | | | | | | | | | |
|---|---|---|---|---|---|---|---|---|---|---|---|
| | 0 | 1 | 2 | 3 | 4 | 5 | 6 | 7 | 8 | 9 | 28 |
| AM | ✓ | | | | ✓ | ✓ | ✓ | ✓ | ✓ | ✓ | ✓ |
| PM | | | | | | | | ✓ | ✓ | ✓ | |

TABLE 2

Dates of breath collection as indicated by ticks) for Cohort 2 treatment with anti-malaria drug Piperaquine. Breath was collected at baseline (day 0 AM), after malaria infection and before administration of anti-malaria (day 0 PM-day 8 AM), after administration ot anti-malaria drug (day 8 PM-day 10 PM) and at the recovery phase (day 29 AM).

| | Day | | | | | | | | | | | |
|---|---|---|---|---|---|---|---|---|---|---|---|---|
| | 0 | 1 | 2 | 3 | 4 | 5 | 6 | 7 | 8 | 9 | 10 | 29 |
| AM | ✓ | | | | ✓ | ✓ | ✓ | ✓ | ✓ | ✓ | ✓ | ✓ |
| PM | | | | | | | | | ✓ | ✓ | ✓ | |

Exhaled Breath Collection

Volunteers were requested to breathe normally and after a few seconds volunteers were asked to breath out a small amount using a "ha" expiration, pause and then continue breathing out as far as they could comfortably perform. For breath collection, volunteers were asked to repeat the "ha" and during the pause to put the cardboard tube between the lips. Volunteers were asked to complete an exhalation into the bag, by breathing out as far as they could comfortably. As soon as they had finished breathing out, they closed the valve (d) (FIG. 1). Neither a nose clip nor a VOC filter were used.

TABLE 3

Summary of events for malaria study in Cohort 1 and 2.

| Cohort | Parasite inoculation | Treatment with test drug | Riamet treatment (rescue drug) | Follow up visit (recovery phase) |
|---|---|---|---|---|
| 1 | Day 0 | Day 7 AM | Day 24 | Day 28 |
| 2 | Day 0 | Day 8 AM | Day 25 | Day 29 |

Adsorption by Solvent Tubes

Two layer sorbent tubes containing 200 mg of TenaxTA and 200 mg of Sulficarb (Markes International Limited, UK) were used. Tubes were exposed to 1 L of the breath sample. The method used to transfer breath volatiles to the tube was by using an electric pump which draws breath sample from the bag and through the tube within 5 min (FIG. 2). Tubes were stored in the fridge at 4° C. until further analysis. Bags containing a small volume of breath were also kept in a cold mom and sent back on ice to Canberra, Australia.

Ambient Air Samples

The method to collect ambient air was as follows, for Cohort 2 an empty bag (the same type of bags used for breath collection) was connected via one of its valves to a sorbent tube and the sorbent tube was then connected to an electric pump. Both valves of the bag were opened to allow ambient air drawn by the pump to go through the bag and the sorbent tube. The flow of the pump was 200 ml/min and ambient air was collected for 5 min. The inventors used a bag to collect ambient air to provide "background" conditions for the breath samples.

For Cohort 1 the inventors used ta similar method as above to collect ambient air but without a bag, instead the pump was connected directly to the sorbent tube.

Exhaled Breath Analysis by Gas Chromatography-Mass Spectrometry

GC-MS analysis of breath samples used sorbent tubes thermally desorbed for 10 min at 280° C. (Unity2, Markes International, UK) and transferred to a cold trap (filled with Tenax TA and Unicarb), held at 30° C. and subsequently heated to 300° C. to minimize band broadening. The split ratios after cold trap applied were 6:1. A gas chromatograph (Bruker 451 Model GC, Bruker Daltonik Inc., USA) using a GC capillary column ZB-5MS (Phenomenex Australia Pty Ltd.) 30 m in length, 0.25 mm ID, and 0.25 μm film thickness was used with the following temperature program: initial temperature of 35° C. for 5 min and held for 5 min, ramped to 250° C. at 5° C./min. The final temperature of 250° C. was held for 2 min. The total run time for the analysis was 50 min. Helium carrier gas at a flow rate of 0.8 ml/min.

A single quadrupole mass detector (Scion SQ, Bruker Daltonik Inc., USA) was set with a full scan detection (scan time=250 ms) covering ion mass range from 35 to 350 m/z with positive polarity.

During GCMS analysis of the samples for Cohort 2 the ion source was contaminated and the sensitivity of the instrument decreased. Therefore, absolute quantitative comparisons between the cohorts were considered to be invalid and data analysis was done separately for each cohort. The results show the same general pattern of volatile organic compounds was detected.

Exhaled Breath Analysis by Electronic Nose

For Cohort 1 only: Direct breath analysis by E-nose was analysed by sampling expired breath directly from bags (FIG. 4). For each sample, 200 ml of breath at a flow rate of 40 ml min$^{-1}$ was analysed.

DiagNose (C-it, The Netherlands) electronic nose consists of seven n type oxides sensors (doped and undoped $SnO_2$ and $WO_3$); one sensor type was present in triplicate, three sensor types in duplicate, and the other three types as single sensors, making an array of 12 sensors in total (Table 4). The sensor array temperature was continuously modulated. Temperature waveforms were generated at a periodicity of 20 seconds and 32 data points were collected during that period. The total analysis time was 5 minutes. The total number of virtual sensors is a combination of sensor number×time steps×thermal loops in one cycle, i.e 12×15×32 equal to 5760 virtual sensors. Each time step represents 20 seconds of analysis. Instrument air, at a flow rate of 400 ml min$^{-1}$ was used as a carrier gas. After each breath analysis the device was purged with instrument air for approximately 35 min to allow baseline recovery.

Breath Spiked with Malaria Biomarker

Pure breath was spiked with allyl methyl sulfide at different concentrations. Pure breath was collected as described above. In this case a single sample represents three breath exhalations (approx. 6 L of breath in total).

TABLE 4

Sensors type in DiagNose.

| Sensor type | Doped | Number of sensors | Sensor ID |
|---|---|---|---|
| SnO$_2$ | Pd | 3 | S3, S4, S5 |
| SnO$_2$ | Pt | 3 | S9, S10, S11 |
| WO$_3$ | — | 2 | S6, S7 |
| SnO$_2$ | +Pd | 1 | S2 |
| SnO$_2$ | Ag | 1 | S1 |
| SnO$_2$ | PtAg | 1 | S12 |
| SnO$_2$ | Cu | 1 | S8 |

Note:
not all bags contained enough breath to perform E-nose analysis in addition to the GC-MS analysis. Sample size was between n = 3 and 7.

The set-up of what the inventors called the patient simulator is shown in FIG. 5. A bag containing 2 L of healthy breath (1) was connected to a micro pump (2) (SP 100EC, Schwarzer Precision). The outlet of the micro pump was attached into the side neck of a two-neck round bottom boiling flask (3). The straight neck of the flask was used as spiking point (4) and at the same time as a mean to transfer spiked/pumped breath to a bag named "spiked breath" (5). To ensure that the bottom of the flask reaches at least 250° C., the flask was placed into a bed with pearls and heated with a hot plate heater (6) (Haines Educational, Australia). When the desired temperature of the flask was reached, 3 µl of allyl methyl sulfide was injected at the spiking point (4) with a gas tight syringe (SGE Analytical Science, Pty Ltd., Australia). The compound was immediately evaporated. Soon after that a pump (2) with a flow of 180 ml/min transferred together pure breath (1) and malaria biomarker to a "spiked breath" bag (5). The pump was stopped when the initial healthy breath bag was emptied. The final allyl methyl sulfide concentration in the "spiked breath" bag was 330 ppm. A dilution is prepared by injecting 300 ml of concentrate spiked breath into a secondary bag filled with 2 L of pure breath to reach a concentration of 43 ppm. Further dilutions were prepared in new individual bags to reach the three final spike concentration levels of 10 ppm, 500 ppb and 10 ppb. This was used to build calibrations curves to estimate absolute concentrations of the volatile organic compound in the breath.

In total, three repetitions for each concentration (pure, 10 ppb, 500 ppb, 10 ppm) were prepared. For each sample a volume of 1 L of either pure or spiked breath was transferred into sorbent tubes for GC-MS analysis. For E-nose analysis samples were analysed directly from the bags.

Chemicals

Allyl methyl sulfide from Sigma-Aldrich (Belgium) and 1-methylthio-propane were purchased from ABCR GmbH & Co (Karlsruhe, Germany). (E)-1-methylthio-1-propene and (Z)-1-methylthio-1-propene were synthesized by Advanced Molecular Technologies Pty Ltd (Melbourne, Australia).

Statistical Analysis

Statistical data analysis was performed in MATLAB (The MathWorks, Natick, Mass.) using standard procedures provided in MATLAB itself and in the MATLAB STATISTICS TOOLBOX. UscramblerX (version 10.2, CAMO software) was used to carry out principal component analysis.

Descriptive Level

Box plots were used to evaluate the differences before and after anti-malaria drug treatment. One-way ANOVA was applied and the function compares the means of the samples and returns the p-value for the null hypothesis that all samples are drawn from the same population. And to further assess whether abundance of volatiles were significantly different before or after anti-malaria treatment we used a multicomparison test (Bonferroni corrected).

Multivariate Analysis

Principal Component Analysis (PCA) was used as dimension reduction technique and to see if there are differences between the different phases of cohort. Data reduction was carried out by means of projection into a PCA subspace. Further multivariate statistical analysis to determine if adding individual volatiles can consistently discriminate samples was subjected to MANOVA, an implementation of the Statistical Toolbox in MATLAB.

Feature Selection in Electronic Nose

The data used to determine best sensors responding to malaria biomarkers were the response differences between breath spiked data described above at 10 ppb (class 2) and the controls breath with 0 ppb (class 1). The approach used for sensor selection was the Q-(F) values. By a feature F we mean a single real-valued measurement extracted from the high-dimensional vector of measurements obtained from the Enose.

Sensors with Q were define the quality indicator q(F) for the quality of any feature F in predicting the class of a set of samples:

q is calculated by taking the quotient of the distance of the means of F across samples of the considered classes by the product of the standard deviations of the individual samples in each class. In the case of two classes, e.g. control (class 1) and infected samples (class 2), this equates to:

$$q(F) = \frac{|\mu_1(F) - \mu_2(F)|}{\sigma_1(F)\sigma_2(F)2}$$

where $\mu_1(F)$ denotes the mean of all values of F for samples of class 1, $\mu_2(F)$ the mean for samples of class 2, and $\sigma_1(F)$ and $\sigma_2(F)$ the corresponding standard deviations. The motivation of this measure is that q(F) is large, whenever the mean values of F in the considered classes differs a lot between classes while the spread of values of F within the classes (the standard deviation) is small. In this situation F is a good feature for distinguishing the classes in question. If, on the other hand, the means of F values in different classes are (almost) the same or the spread of values of F within each of the classes is very large, q is (close to) zero. In that case, F is not a good feature for distinguishing the classes. Generally values of q are in the interval [0,∞] with values at least greater than 1 indicating that F may be useful for classification.

For this study sensors with q-values higher than five were considered to be the most informative sensors and potential discriminator of the two classes.

Classification

Two common classifiers, a support vector machine and k nearest neighbour algorithm, were trained to classify samples, using "leave one out" cross-validation the results (Wang et al., 2014):

1) A support vector machine (SVM) (Cortes and Vapnik, 1995) constructs a hyperplane to separate training data in to different classes. We used the libsvm library (Lin, 2011) to perform the classification using C-SVC (SVM classification with cost parameter of C). Two types of SVM were used: linear and a nonlinear SVM using Gaussian radial basis kernel function. The Gaussian radial basis kernel function is, $k(x_i, x_j) = \exp(-\gamma \|x_i, x_j\|^2)$, where $x_i$ is the vector of the data for sample i and $\gamma$ is the kernel width. The inventors selected $\gamma$ using the inverse of number of features (the default $\gamma$ value in libsvm) as previous studies showed this gives the best classification performance (Wang et al., 2014). The inventors found radial SVM performs much better than linear SVM for this data set, thus we report here classification results using radial SVM with C=256.

2) The k nearest neighbour (kNN) algorithm compares the input data with an existing set of training data by computing a distance metric (Russell and Norvig, 1995). The neighbours of the input data are the k data points with the smallest distance metric. The input data's class is determined to be that with the most data points in the neighbourhood. The inventors tested the neighbourhood size for k={1, 3, 5, 7}. The maximum value of k is set at 7 since there are at most 7 samples of each class in the data set, so there will be at most 7 samples of the same class in the training data that can appear in the neighbourhood of any test data. The inventors report here results for k=1 as there are no significant difference between the different k values.

Cross-Validation

The inventors performed two types of cross-validation with the data set. For each individual trial, the inventors performed one-against-all (leave-one-out) cross-validation. That is, the full data sets for each trial were partitioned into N pairs of a training set (of N−1 data samples) and a test set (of the remaining 1 data sample), where N is the size of the data set. This process was repeated N times to cover all the data in the set. The classifiers were trained using the training set and then applied to the test set.

In addition to the one-against-all cross-validation, the inventors trained the classifiers using the data from one of the cohorts, and test on the data on the remaining cohort. For the purpose of this test, the data were normalised using the blank sample of the day of analysis (i.e. analysis of an empty sorbent tube), as the GC-MS sensitivity changed between the two cohorts.

PCR Quantification of P. falciparum Parasitemia

A consensus *Plasmodium* species RT-PCR method described elsewhere (McCarthy et al., 2013) was modified to make use of TaqMan hydrolysis probe chemistry. This PCR assay was designed to amplify a conserved 199-base pair (bp) target of the multicopy and a highly conserved 18S ribosomal RNA gene. Parasites were quantified from 500 μL of packed red cells. Each sample was tested in duplicate during the study. After completion of the study, all samples were retested in triplicate. When coefficients of variation varied by >20%, samples were tested again.

Volatile Collection from Cell Culture.

Headspace collection was performed using the same type of sorbent tubes used for breath collection. The lids of the flaks were modified so that a sorbent tube can be connected. The tubes were connected at one end to the tube and at the other end to an electric pump (FIG. 3S) and 200 ml of headspace was transferred to the tube at 200 ml min$^{-1}$. The system is not hermetically closed so a dilution effect (air from ambient also entered the system) occurs while collecting the headspace; this was done to allow collecting enough volume for GC-MS analysis. Tubes were stored at 4° C. until analysis. Ambient air samples were also collected at the time of analysis to check if target compounds did not come from the environment.

Example 2—Volatile Organic Compounds with Increased Levels in Patients with a *Plasmodium* Infection Using gas chromatography-mass spectrometry it was observed that there are nine compounds that change after malaria infection and after anti-malaria drug injection (Table 5).

The four sulfur compounds allyl methyl sulphide, 1-methylthiopropane, (E)-1-methylthio-1-propene and (Z)-1-methylthio-1-propene have very similar patterns while the other compounds listed in Table 5 have a variety of patterns. Although all nine volatiles showed changes, analysis is focused on the four sulfur derived VOCs because (1) in some volunteers these compounds were absent or at levels not detectable at Day 0 and (2) the compounds seem to move as a group indicating some possible links in their biochemical pathways.

Chromatograms of three of the sulfur compounds allyl methyl sulfide, (E)-1-methylthio-1-propene and (Z)-1-methylthio-1-propene and their changes over the course of the cohort are shown in FIG. 6 and FIG. 7 (Cohort 1 and 2 respectively).

Example 3—Statistical Analysis

Cohort 1
Multivariate Analysis

Figure 8A:
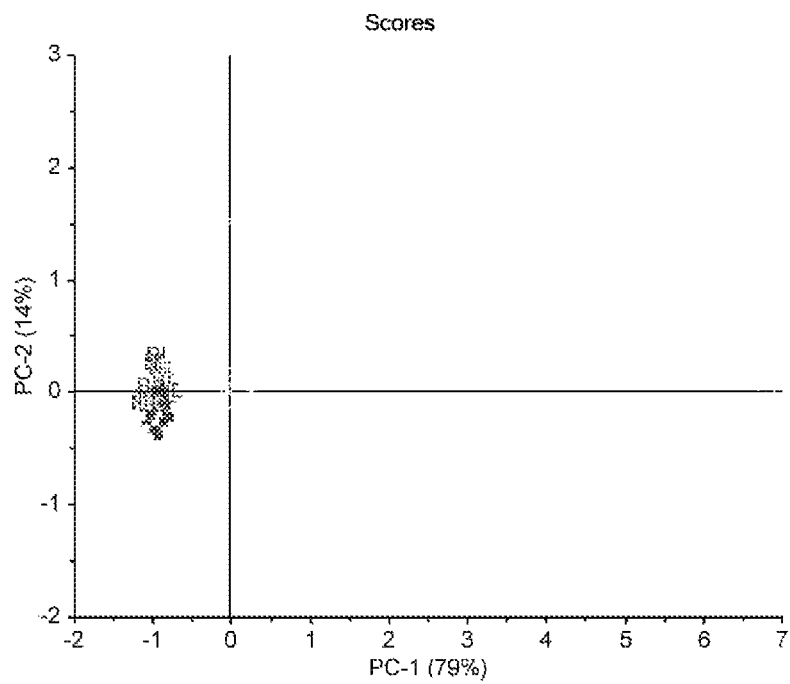
Figure 8B:
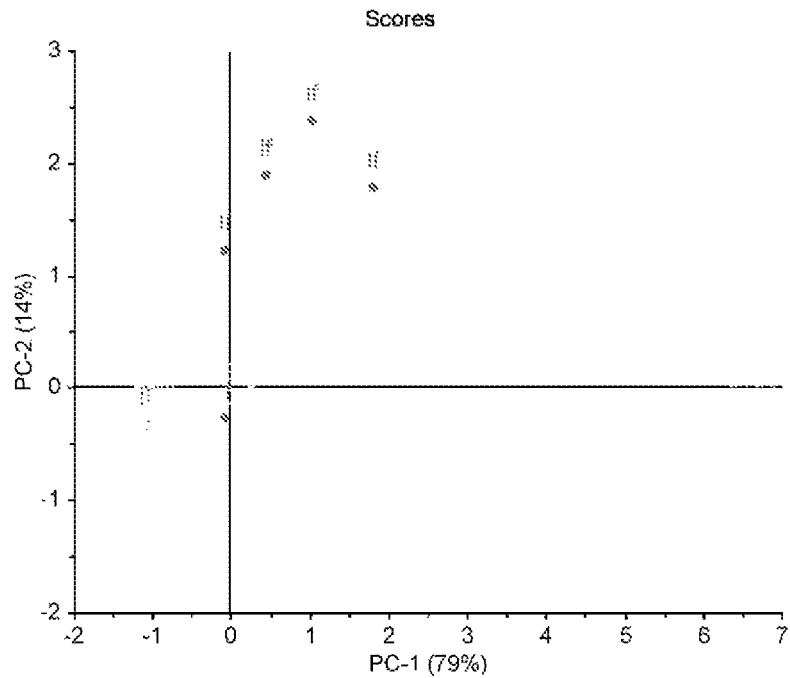
Figure 8C:
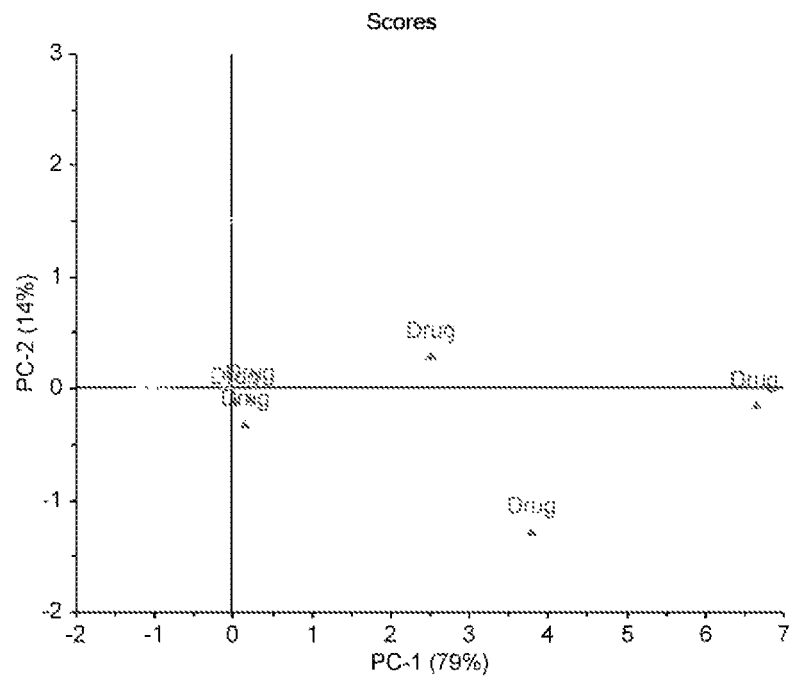
Figure 8D:
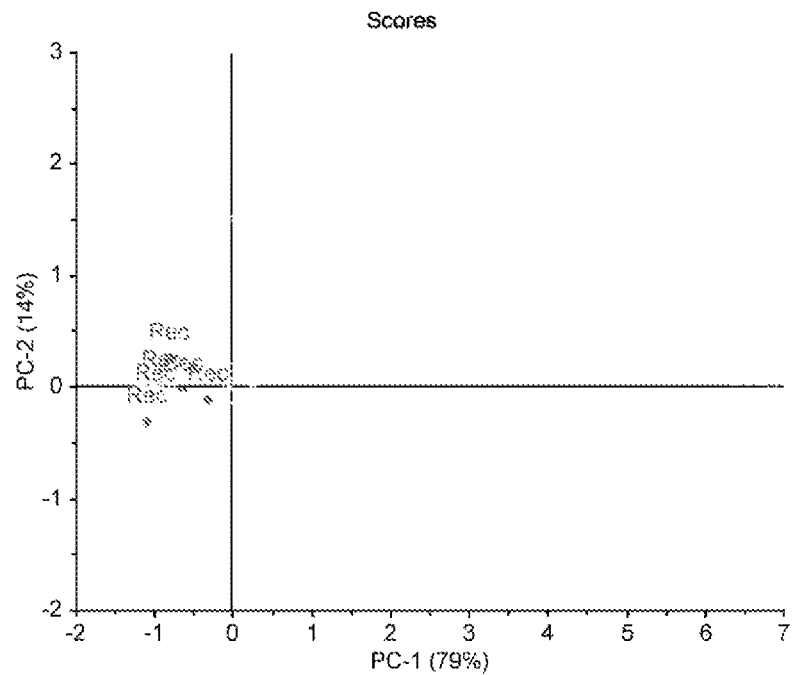
Figure 8E:
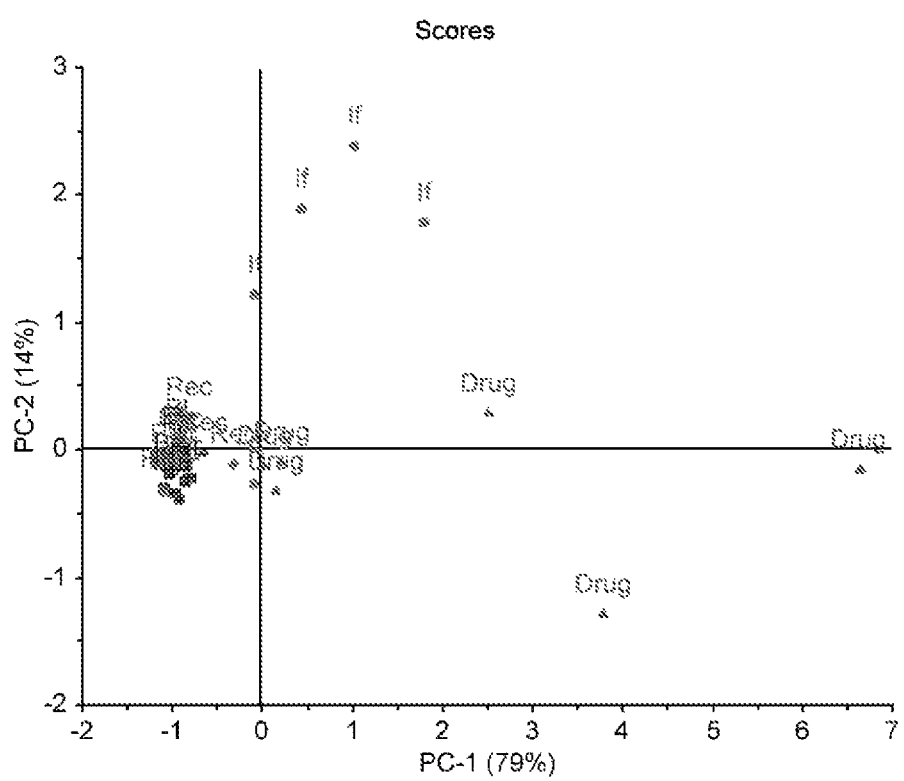

In order to visualise changes after malaria infection and drug administration, PCA was performed for all individuals and for all four thioethers (FIG. 8a to 8e). For clarity of the plot, samples from Day 0 (FIG. 8a), 7 AM (FIG. 8b), 7 PM (FIG. 8c) and 28 (FIG. 8d) only were used in PCA. It can be observed that there is a clear discrimination among the stages and that the VOCs provide evidence that there are changes in breath after malaria infection (FIG. 8e).

TABLE 5

Malaria biomarkers in breath, retention time and characteristic mass to charge ratio used for semi-quantifications.

| RT (min) | Compound name | m/z | Molecular weight |
|---|---|---|---|
| 1.99 | Carbon dioxide | 44 | 44 |
| 2.2 | Isoprene | 67 | 68 |
| 2.21 | Acetone | 58 | 58 |
| 3.28 | Benzene | 78 | 78 |
| 3.77-3.9 | Allyl methyl sulfide | 88 | 88 |
| 4.09 | 1-Methylthio-propane | 90 | 90 |
| 4.30 | (E)-1-Methylthio-1-propene | 88 | 88 |
| 4.76 | (Z)-1-Methylthio-1-propene | 88 | 88 |
| 10.44 | Cyclohexanone | 85 | 98 |

Descriptive Level

Box plots for each compound across the different days of breath collection were calculated using the area under the peak (FIG. 9). ANOVA test indicates that there are significant differences in the abundance means of the compounds across breath collection days (stages of malaria). In particular Day 7-PM which is the sample collected about 6.5 hours after anti-malaria drug showed the highest increase in concentration.

The largest significant change in breath composition is shown with (Z)-1-Methylthio-1-propene (FIG. 9). The multicomparison test for (Z)-1-Methylthio-1-propene (FIG. 10) showed that there were significant higher levels of the compound (no overlapping intervals) on Day 7-PM which is a sample collected 6.5 hours after anti-malaria administration.

Multivariate Analysis of Variance (MANOVA)

Samples collected at Day 0 AM and Day 7 PM were subjected to MANOVA using all four breath malaria biomarkers (allyl methyl sulfide, 1-methylthiopropane, (Z)-1-methylthio-1-propene and (E)-1-methylthio-1-propene), subsequently one compound was removed at a time and MANOVA was performed again to find out if the differences were still significant. The results show that the differences were significant even with only two compounds (Table 6), being (Z)-1-methylthio-1-propene the compound that provides the largest differences.

TABLE 6

Compounds (variables) used to perform MANOVA and the significance of the test for Cohort 1. Data employed for analysis was from Day 0 AM and Day 7 PM.

| Variable used for MANOVA | p-value |
|---|---|
| (Z)-1-Methylthio-1-propene + (E)-1-Methylthio-1-propene + 1-Methylthiopropane + allyl methyl sulfide | 0.0031 |
| (Z)-1-Methylthio-1-propene + (E)-1-Methylthio-1-propene + 1-Methylthiopropane | <0.0001 |
| (Z)-1-Methylthio-1-propene + (E)-1-Methylthio-1-propene | <0.0001 |

Cohort 2

In Cohort 2 breath samples from seven individuals were collected, however one individual was excluded from the data analysis as this individual was unable to perform the "ha' expiration- to exclude the alveolar air, which affected the total chromatographic profile (a dilution effect of the sample=alveolar air+pulmonary air). Data analysis shown below is therefore from six individuals.

Multivariate Analysis

Figure 11A:
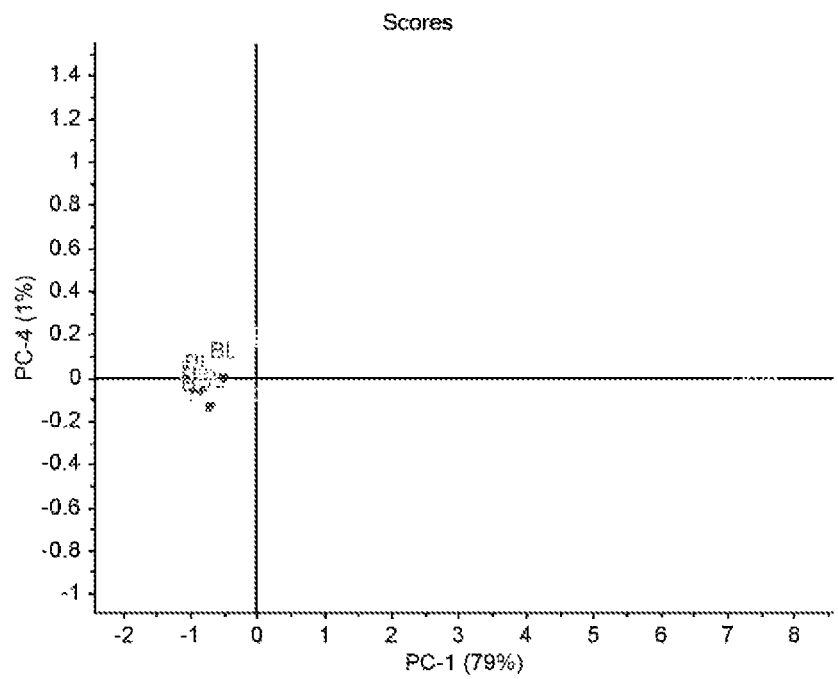
Figure 11B:
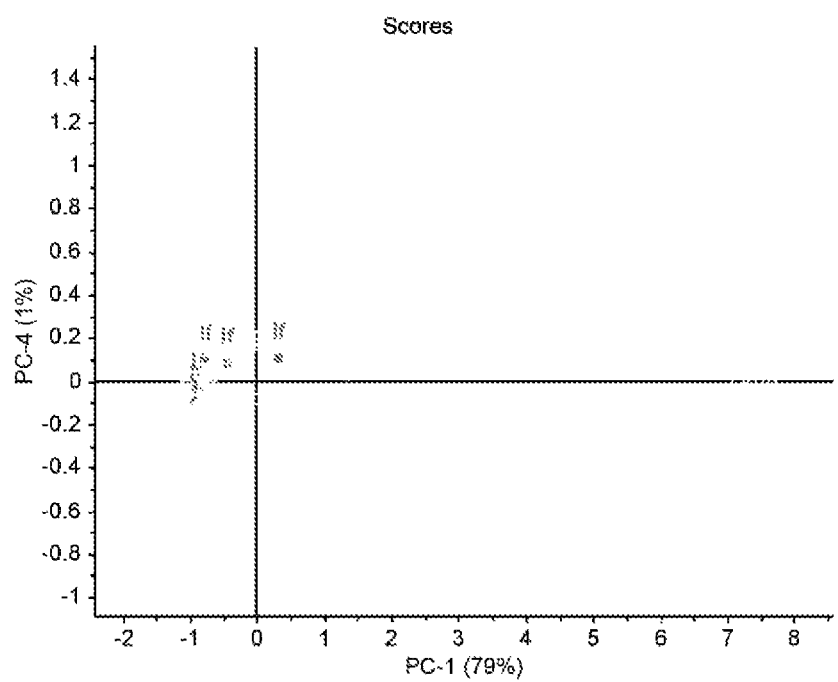
Figure 11C:
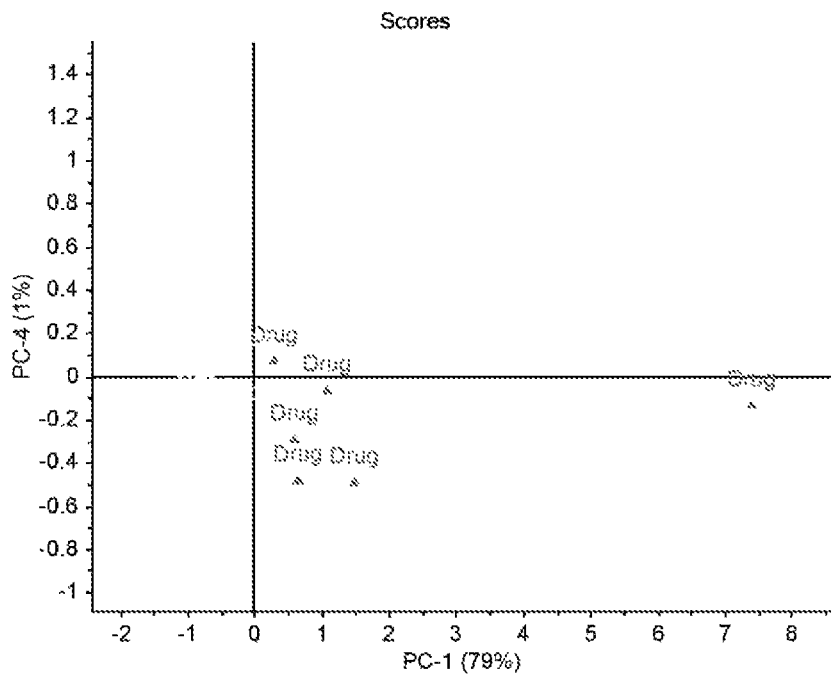
Figure 11D:
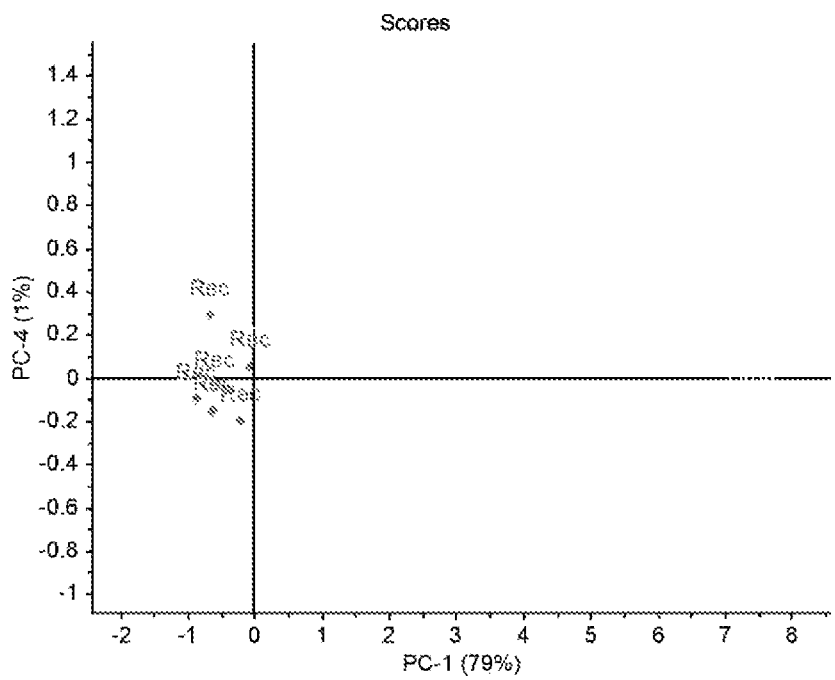
Figure 11E:
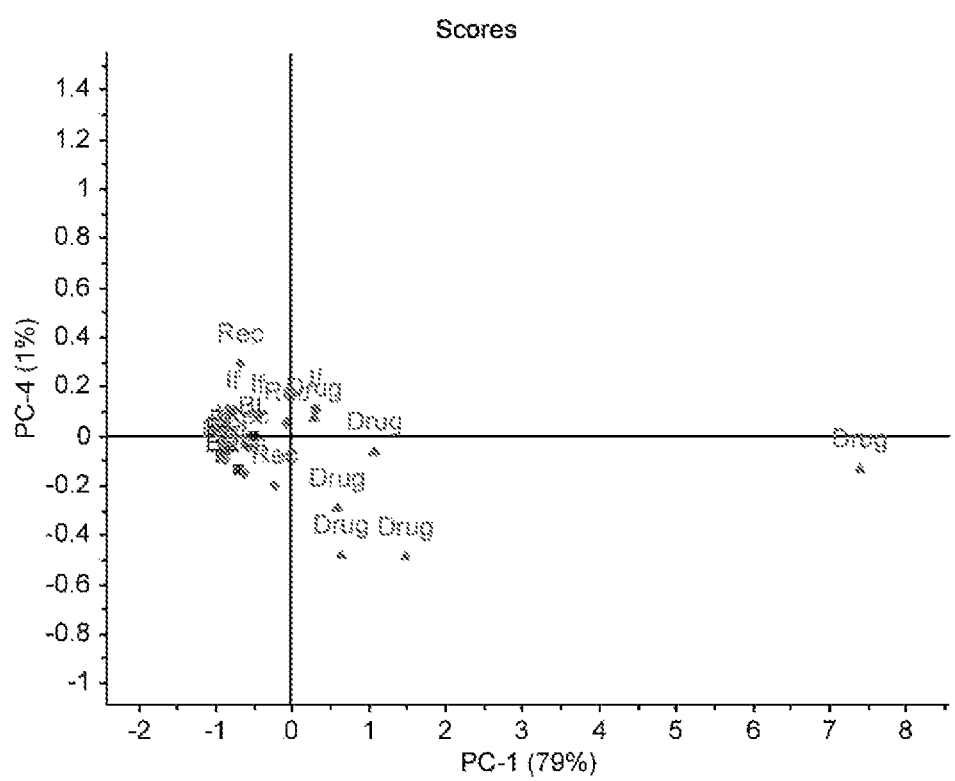

In order to visualise changes after malaria infection and drug injection, Principal Components Analysis (PCA) was performed for all individuals and for all four thioethers (allyl methyl sulfide, 1-methylthiopropane, (Z)-1-methylthio-1-propene and (E)-1-methylthio-1-propene) (FIG. 11a to 9e). For clarity of the plot, samples baseline Day 0 (BL) (FIG. 11a), during malaria infection Day 6 (If) (FIG. 11b), after anti-malaria administration Day 8-PM (Drug) (FIG. 11c) and at recovery phase Day 29 (Rec) (FIG. 11d) only were used in PCA. It can be observed that there is a clear discrimination among the stages and that the VOCs provide evidence that there are changes in breath after malaria infection (FIG. 11e).

Descriptive Level

Box plots (FIG. 12) for each compound across the different days of breath collection. ANOVA test indicates that there are significant differences in the mean abundance of the compounds across breath collection days (stages of malaria). In particular Day 8-PM which is the sample collected about 6.5 hours after anti-malaria drug showed the highest increase in concentration.

The largest significant change in breath composition is shown with (Z)-1-Methylthio-1-propene (FIG. 12). The multicomparison test for (Z)-1-Methylthio-1-propene (FIG. 13) showed that there were significantly higher levels of the compound (no overlapping intervals) on Day 7 PM, which is a sample collected 6.5 hours after anti-malaria administration.

Multivariate Analysis of Variance (MANOVA)

Samples collected at Day 0 and Day 8-PM were subjected to MANOVA using all four breath malaria biomarkers, subsequently one compound was removed at a time and MANOVA was performed again to find out if the differences were still significant. The results show that the differences were significant even with only two compounds (Table 7), being (Z)-1-methylthio-1-propene the compound that provides the largest differences.

In both Cohorts 1 and 2, the effect of the drug could be detected within 6.5 hours of drug administration.

TABLE 7

Volatile organic compounds (variables) used to perform MANOVA and the significance of the test for Cohort 2. Data employed for this analysis was from Day 0 and Day 8-pm.

| Variable used for MANOVA | p-value |
|---|---|
| (Z)-1-Methylthio-1-propene + (E)-1-Methylthio-1-propene + 1-Methylthiopropane + allyl methyl sulfide | <0.0001 |
| (Z)-1-Methylthio-1-propene + (E)-1-Methylthio-1-propene + 1-Methylthiopropane | 0.0028 |
| (Z)-1-Methylthio-1-propene + 1-Methylthiopropane | 0.0227 |

Example 4—Detecting Volatile Organic Compounds by Electronic Nose (DiagNose)

The present inventors have also shown that an electronic nose can be used to detect the VOCs. The present inventors have also shown that the electronic nose can discriminate breath containing higher levels of these compounds from breath with lower, or zero, levels of these compounds. In contrast to GC-MS analysis, samples were analysed directly from the bag.

The present inventors found that different patterns of VOCs were observed at each day of breath collection (FIG. 14). For example, the day after administration with an antimalarial results in a higher sensor response when compared to baseline and malaria infection period.

The inventors used Q-values to select the most sensitive sensors to allyl methyl sulfide, (FIG. 15) and the method provided 118 virtual sensors out of 5760 sensors as able to discriminate allyl methyl sulfide in breath samples (Table 8). It can be seen in FIG. 15 that the area with the largest distance was the top right side of the plot which correspond to sensor 1 ($SnO_2$ doped with Ag).

TABLE 8

Best virtual sensors able to discriminate control breath from spiked breath with allyl methyl sulphide.

| |
|---|
| 858 |
| 1017 |
| 1937 |
| 2163 |
| 2314 |
| 2315 |
| 2317 |
| 2322 |

TABLE 8-continued

Best virtual sensors able to discriminate control breath from spiked breath with allyl methyl sulphide.

| |
|---|
| 2657 |
| 2692 |
| 2699 |
| 2701 |
| 2703 |
| 2919 |
| 2936 |
| 3041 |
| 3057 |
| 3074 |
| 3075 |
| 3077 |
| 3080 |
| 3081 |
| 3087 |
| 3090 |
| 3425 |
| 3441 |
| 3442 |
| 3457 |
| 3458 |
| 3461 |
| 3463 |
| 3469 |
| 3470 |
| 3472 |
| 3473 |
| 3474 |
| 3475 |
| 3488 |
| 3692 |
| 3809 |
| 3824 |
| 3825 |
| 3840 |
| 3841 |
| 3842 |
| 3846 |
| 3853 |
| 3854 |
| 3856 |
| 3857 |
| 3859 |
| 3872 |
| 4070 |
| 4076 |
| 4193 |
| 4209 |
| 4210 |
| 4225 |
| 4226 |
| 4230 |
| 4231 |
| 4238 |
| 4239 |
| 4240 |
| 4241 |
| 4242 |
| 4243 |
| 4256 |
| 4577 |
| 4594 |
| 4612 |
| 4614 |
| 4615 |
| 4616 |
| 4617 |
| 4621 |
| 4624 |
| 4625 |
| 4626 |
| 4627 |
| 4639 |
| 4640 |
| 4843 |
| 4978 |
| 4992 |
| 4993 |
| 4994 |
| 4995 |
| 4998 |
| 4999 |
| 5001 |
| 5002 |
| 5004 |
| 5006 |
| 5008 |
| 5009 |
| 5010 |
| 5011 |
| 5023 |
| 5024 |
| 5377 |
| 5378 |
| 5379 |
| 5380 |
| 5382 |
| 5383 |
| 5388 |
| 5389 |
| 5390 |
| 5392 |
| 5393 |
| 5394 |
| 5395 |
| 5396 |
| 5407 |
| 5408 |
| 5729 |
| 5746 |

Box plots (FIG. 16) for sensor number 2314 (the sensor with the largest distance) across the different days of breath collection. ANOVA test indicates that there are significant differences in the response of the sensor across breath collection days (stages of malaria). In particular Day 0 was significantly different from samples collected after drug treatment.

The multicomparison test for sensor 2314 (FIG. 17) confirms there were significant higher sensor response (no overlapping intervals) on Day 8 and 9 (AM and PM).

Example 5—Levels of Volatile Organic Compounds

Overlay of GCMS spectra of breath sample collected 6.5 hours after anti-malaria injection and calibration curves for the spiked breath samples (FIG. 19) confirm that the VOC at ~RT 3.75 is allyl methyl sulfide.

The absolute concentrations for allyl methyl sulphide (AMS) were calculated for Cohort 2 (Table 9) by using the linear equation obtained from calibration curve. The equation used is as follows:

$$Y = 3E\text{-}07_x$$

where x is the area under the peak and y the calculated concentration in ppb. The values calculated in Table 9 are approximations only as the concentrations of the prepared standards were not very near the expected the concentration of the analyte in the unknown.

TABLE 9

Approximate absolute concentrations of allyl methyl sulphide in breath samples from Cohort 2.

| COHORT 2 | ppt |
|---|---|
| Day 0 | 11.18 |
| Day 4 | 39.16 |
| Day 5 | 0.23 |
| Day 6 | 96.90 |
| Day 7 | 12.16 |
| Day 8 AM | 61.96 |
| Day 8 PM | 308.54 |
| Day 9 AM | 100.59 |
| Day 9 PM | 127.88 |
| Day 10 AM | 32.95 |
| Day 10 PM | 30.26 |
| Day 29* | 84.53 |

*There was an outlier at Day 29 and the data point was withdrawn from calculations.

The detection of >15 ppt of AMS is indicative of malaria infection and a spike of over 300 ppt indicates treatment success.

Table 10 and Table 11 show that the highest fold change, ratio between area under the curve Day X/Day 0 (wherein (X=a day different from 0) for each of the volatile organic compounds (allyl methyl sulfide, 1-methylthiopropane, (Z)-1-methylthio-1-propene and (E)-1-methylthio-1-propene) and across cohorts is sample collected 6.5 h after drug administration (in bold). There is one exception, for compound AMS in Cohort 1 where the highest change is at Day 4.

TABLE 10

Fold changes for Volatile Organic Compounds Cohort 1.

| VOC | ZMP | AMS | MP | EMP |
|---|---|---|---|---|
| Day 0 | | | | |
| Day 4 | 19839.5 | 11251.9 | 21063.6 | 6080.0 |
| Day 5 | 10182.5 | 1914.5 | 3975.4 | 2462.6 |
| Day 6 | 9599.9 | 3642.3 | 2862.3 | 4905.2 |
| Day 7 AM | 12323.2 | 2865.5 | 9371.8 | 2975.7 |
| Day 7 PM | 169520.0 | 1906.4 | 24688.1 | 8459.5 |
| Day 8 AM | 13530.3 | 905.2 | 10953.6 | 2609.0 |
| Day 8 PM | 19163.4 | 7075.1 | 2557.8 | 1163.6 |
| Day 9 AM | 2532.1 | 1081.5 | 1573.0 | 672.8 |
| Day 9 PM | 5624.5 | 1389.7 | 1608.1 | 670.0 |
| Day 28 | 2581.4 | 893.6 | 2083.1 | 520.0 |

The inventors expect that this fold change values may be higher in field acquired malaria patients where parasitaemia would be between 0.1%-10%. The present samples were collected from a pilot induced blood-stage *Plasmodium falciparum* infection in which volunteers were infected with a low dose and the infection was limited to 0.001% parasitaemia, A rise in fold change was observed on Day 28/29, this could be due to the treatment of Riamet (the rescue drug) just four days before sample collection.

Example 6—Differential Diagnosis

Sulfide compounds are universal bacterial metabolites in vitro (e.g. dimethyl sulfide). In order to exclude the possibility that the identified VOCs are general indicators of infection and not selective for malaria, the present inventors re-examined the breath chromatograms of patients presenting at hospital emergency departments with bacterially-induced fevers. They found that the levels of each of allyl methyl sulfide, 1-methylthiopropane, (Z)-1-methylthio-1-propene and (E)-1-methylthio-1-propene were very low and the same in fever and control groups The microorganisms in these febrile non-malarial patients were identified as *Escherichia coli, Staphylococcus aureus, Finegoldia magna, Candida albicans, Streptococcus agalactiae, Streptococcus pyogenes*.

TABLE 11

Fold changes for Volatile Organic Compounds Cohort 2.

| VOC | ZMP | AMS | MP | EMP |
|---|---|---|---|---|
| Day 0 | | | | |
| Day 4 | 179.0 | 1097.6 | 296.2 | 65.7 |
| Day 5 | 2.7 | 9.5 | 0.6 | 3.2 |
| Day 6 | 5.4 | 3250.5 | 1.1 | 257.3 |
| Day 7 | 129.9 | 106.4 | 162.3 | 93.6 |
| Day 8 AM | 169.7 | 2434.0 | 1.1 | 4.4 |
| Day 8 PM | 10445.4 | 11555.1 | 6386.1 | 2860.8 |
| Day 9 AM | 1609.5 | 3340.1 | 1613.0 | 640.2 |
| Day 9 PM | 4487.8 | 4693.3 | 2336.9 | 216.8 |
| Day 10 AM | 726.5 | 905.8 | 859.2 | 426.5 |
| Day 10PM | 684.8 | 984.9 | 281.6 | 108.3 |
| Day 29 | 1072.3 | 2911.1 | 805.0 | 560.8 |

ZMP=(Z)-1-Methylthio-1-propene, AMS=Allyl methyl sulphide, MP=1-Methylthio propane, EMP=(E)-1-Methylthio-1-propene It should be noted that the volume of breath taken for the above trial from patients with bacterial infection was half the volume (0.5 L) used for the malaria trial (1 L) but, given the noticeable intensities of the peaks after drug treatment, one can be confident those thioethers were not substantially present, even at lower volume of breath analysed.

These results indicate that the detection of the levels of one or more of the VOCs selected from allyl methyl sulfide, 1-methylthiopropane, (Z)-1-methylthio-1-propene and (E)-1-methylthio-1-propene, can be used to identify malaria as the cause of infection. Allyl methyl sulfide is also known to arise from garlic consumption. The inventors considered whether dietary sources of the level of the compound could confound a malaria diagnosis. The results of a test undertaken by the inventors showed that even after consumption of a meal with high garlic content, the levels of allyl methyl sulfide on the breath were much lower than those observed in the clinical trial volunteers.

Figure 18B:
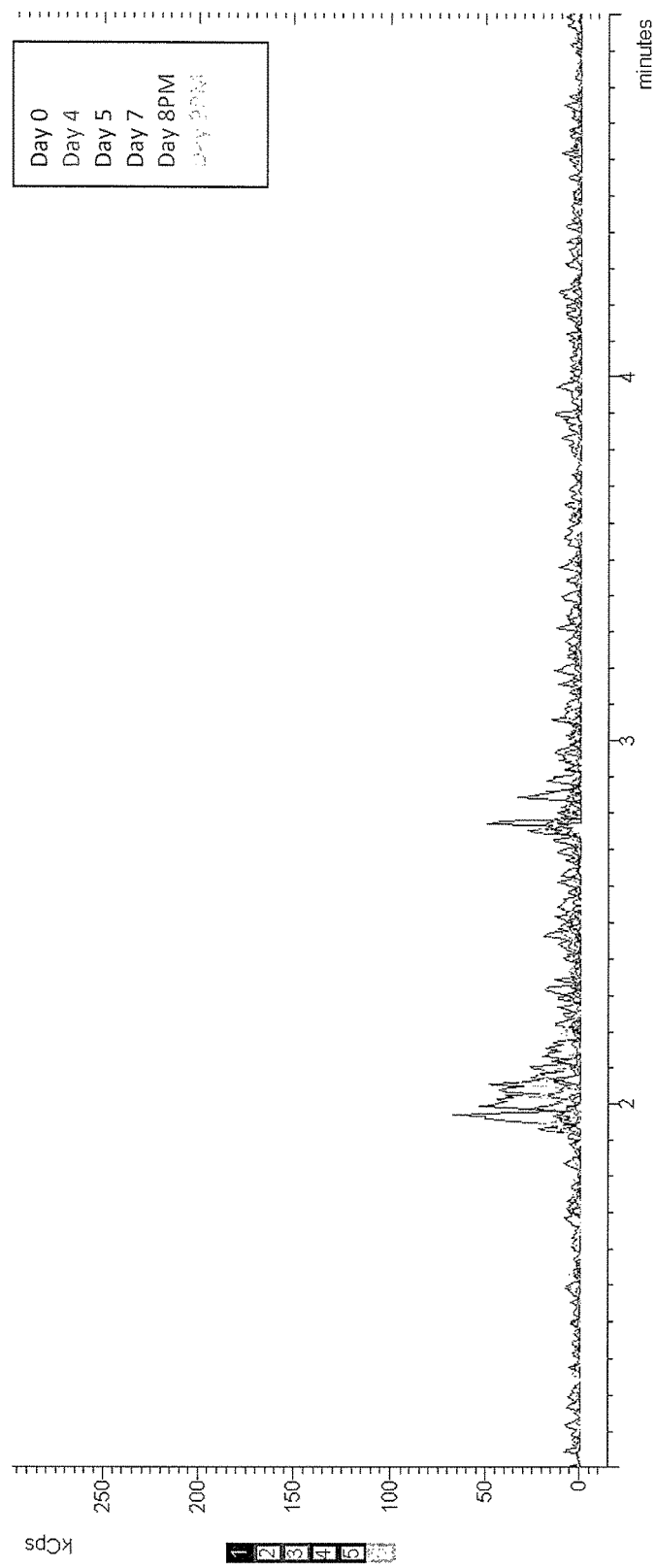

GCMS analysis of ambient air showed no significant peaks for the thioethers (Z)-1-methylthio-1-propene, allyl methyl sulfide and (E)-1-methylthio-1-propene in room air from the clinic (FIG. 18a) indicating the absence (at detectable levels of these VOCs in ambient air samples. Similar results were obtained for 1-methylthio propane (FIG. 18b).

Example 7—Volatiles in Breath are Correlated with Parasite Levels

Results

The inventors investigated the relationship between thioether levels and the level of parasitaemia. Before treatment, there was evidence of cyclical changes in both the levels of thioethers, particularly allyl methyl sulfide and (E)-methylthio-1-propene and the levels of parasitaemia (FIG. 20). In both cases the period appeared to be approximately 48 hours, albeit the sampling regime did not allow any greater resolution, and was imposed on a general rising trend of parasitaemia, as determined by PCR, and levels of thioethers. The cyclical variation in thioether level appeared to be out of phase with the parasitaemia. Phase-shifting the thioether data backwards by 24 hours, revealed a direct correlation between the parasitaemia and volatile levels (FIG. 21a). For Cohort 1, allyl methyl sulfide and (E)-methylthio-1-propene were the compounds with the highest correlations, $r^2=0.94$ and $r^2=0.97$ respectively. For Cohort 2, allyl methyl sulfide was again highly correlated to parasitaemia ($r^2=0.97$) along with 1-methylthio-propane ($r^2=0.92$).

In both cohorts it was observed that the highest levels of thioethers were seen in the first breath sample collected (6.5 hours) after drug administration (FIG. 20), possibly indicating a role for parasite death or lysis in driving thioether production. Volatile levels declined monotonically after initial drug treatment, correlating with clearance of parasitaemia, (FIG. 20). For Cohort 1, administration of a fast acting synthetic ozonide resulted in a faster decline in parasitaemia and thioether levels compared to the clearance observed with the slower acting bisquinoline 4-aminoquinoline in Cohort 2 (FIG. 20). For Cohort 1, post-treatment, there was a direct correlation between levels of parasitaemia and the abundance of (Z)-methylthio-1-propene ($r^2=0.76$), (E)-methylthio-1-propene ($r^2=0.98$) and 1-methylthio-propane ($r^2=0.99$) (FIG. 3b). For Cohort 2, there was a lower but still marked correlation between the levels of thioethers and the levels of parasitaemia, specifically $r^2>0.79$ for (E)-methylthio-1-propene and $r^2>0.76$ for allyl methyl sulfide (FIG. 21b).

Discussion

The 24 hours phase-shift observed between parasite and volatile levels suggest that the volatiles may be linked to the 48 hour lifecycle of the blood-stage parasite, with the peak corresponding to when the infected red blood cells burst (schizont rupture) to release merozoites and infect new red blood cells to begin the erythrocytic cycle again. Schizont rupture occurs every 48 hours in *P. falciparum* infections.

Example 8—Machine Learning Classification of Malaria Infection Based on Thioether Levels Using areas under the peak for the four thioethers present in breath samples from Day 0 pre-infection and Day 7/8 PM, it was found that using leave-one-out cross-validation with a support vector machine (SVM) or k nearest neighbor (KNN) classifier, all samples could be perfectly classified based on the volatile levels, demonstrating statistically significant differences at baseline and soon after drug administration. Ideally it would be possible to train a classifier on one cohort and use it to classify the other cohort. This was complicated somewhat by the fact that the inventors GC-MS ion-source had been cleaned and recalibrated between the two cohorts. However, after performing data normalisation to account for these changes, the inventors trained the classifiers using the Cohort 1 data, and they were able to perfectly classify the data from Cohort 2. In the same way using Cohort 2 to train the classifiers give perfect classification of Cohort 1 data.

Example 9—Volatiles In Vitro

Wong et al. (2012) previously reported that no change in headspace volatiles could be detected when an in vitro erythrocyte culture was infected with *P. falciparum*. The inventors specifically searched for the four thioethers in the headspace of 100 mL of a red blood cell suspension (1% haematocrit, starting parasitaemia 0.5%) exhibiting final parasitaemia levels of about 39%. Thioethers were also not detected in headspace of *P. falciparum* infected cell cultures (5.5 h) following treatment with 1000 ng ml$^{-1}$ of the antimalarial piperaquine tetraphosphate tetrahydrate, nor after treatment with a detergent to disrupt cell membranes. As a positive control, the inventors spiked the four thioethers into the red blood cell cultures at the following levels: allyl methyl sulfide: 2.7 nmol L$^{-1}$, 1-methylthio-propane: 4.4 nmol L$^{-1}$, i.e. values previously detected in healthy individuals (Mochalski et at, 2013), and 2.5 nmol L$^{-1}$ for each of the isomers (Z)-methylthio-1-propene and (E)-methylthio-1-propene. The inventors then incubated the sample for four days and collected headspace as normal. All of the thioethers were readily detected. The in vitro samples also showed VOCs derived from the plastic flask but they did not interfere with detection of the four thioethers, moreover no thioethers were detected in the ambient samples collected.

The biomass of parasitised red blood cell (RBC) present in the blood cultures (0.1 L×0.01 haematocrit×0.39 parasitaemia=0.39 g of infected erythrocytes) were approximately 18 fold higher than the biomass of infected RBC present in the volunteers (5 L×0.43 haematocrit×0.00001 parasitaemia=0.02 g of infected red blood cells). Approximately 200 mL of the available 400 mL of headspace was sampled in vitro, compared with the 1 liter of breath sampled from volunteers. In a human volunteer, there is the potential to "blow off" the thioethers in every breath, so it must be assumed that the levels of thioethers measured in volunteers represent a temporal equilibrium between generation and dissipation, whereas there is significant potential for accumulation of thioethers in the closed flasks used for our in vitro studies. These considerations suggest that the in vitro protocol should be capable of detecting the thioethers, if indeed they are generated at comparable levels to in vivo.

These results suggest that host response is involved in the production of volatiles during the schizont rupture. In the same way the interaction between parasite toxins released during lysis of infected RBCs (schizont rupture) and phagocytic human cells culminate in malarial febrile episodes, other molecular events could take place during schizont rupture that generates the thioethers.

Example 10—Volatile Organic Compounds with Increased Levels in a Patient with a *Plasmodium vivax* Infection Methodology A volunteer was inoculated on Day 0 with ~100 viable *P. vivax*-infected human erythrocytes administered intravenously. On an outpatient basis, the volunteer was monitored by phone daily until Day 7 when they visited the clinical unit daily for blood collection, and then after detection of parasites twice daily (AM and PM) for:

Quantification of parasitemia (as assessed by PCR of both parasite genome equivalents and for the gametocyte-specific transcript Pvs25), The unexpected early onset of symptoms or signs suggestive of malaria, and Adverse events.

During the three or four days leading up to the commencement of treatment (~days 11, 12, 13 and 14,) transmission studies were undertaken. On those days, 2×6 ml of blood was collected (AM and/or PM) into a heparinized vacutainer tube for membrane feeding assays with *An. Stephensi*. Additional blood was collected for other purposes (PCR for parasite quantification, exploratory research bloods and safety bloods as required). To prevent premature exflagellation, blood was kept at 38° C. (for up to 35 minutes) until dispensed into membrane feeders. The volunteer was then escorted to the quarantine insectary facility at Queensland Institute of Medical Research and were asked to allow vector mosquitoes to feed on the volar surface of their forearms or thighs for a period of 10±5 minutes (direct feeding assay). The experimental infection of mosquitoes by direct feeding of participants was performed up to 3 times and by artificial membrane feeding up to 6 times until antimalarial treatment commenced. Additional mosquito feeding by membrane only were undertaken on evening samples collected at the Q-Pharm clinical site.

On the day designated for commencement of treatment, as determined by clinically manifested malaria infection (expected to be ~Day 14), the volunteer was admitted to the study unit and confined for safety monitoring and antimalarial treatment. The trigger for admission to the clinical unit will be positive parasitaemia and the onset of clinical features of malaria, anticipated to occur on ~day 14 based on our previous study (McCarthy et al., 2013). A single finger prick test was performed prior to treatment to compare gametocyte counts with the peripheral blood sample.

Following treatment, the volunteer was followed up as an inpatient for 36 hours to ensure tolerance of therapy and clinical response. Once clinically well, they were followed up on an outpatient basis for continued dosing of antimalarial drug, safety and clearance of malaria parasites as assessed by sensitive quantitative PCR.

In addition to blood collection, breath samples were collected prior to inoculation and up to 14 times post infection. At pre-specified time points, the volunteer was asked to breathe out (up to three times) through a single mouthpiece attached to a breath reservoir (bag). The breath sample was transferred to a sorbent tube and then analysed by gas chromatography-mass spectrometry as described herein to evaluate the presence of volatile organic compounds.

For metabolic studies, a first morning urine void was collected prior to inoculation and 24 hrs after commencement of antimalarial treatment.

Follow up visits for safety assessments were performed on day 28 after malaria challenge and the volunteer was required to be contactable and available up to 2 weeks following this end of study visit.

Riamet® tablets (Artemether (20 mg) and Lumefantrine (120 mg)) 4 tablets orally as a single dose twice a day with fatty food at time 0, 12, 24, 36, 48 and 60 hours, making a total dose of 24 tablets in 6 doses, were used as a rescue treatment.

Results

It can be observed that the kinetics of growth and clearance of *P. vivax* parasitemia is different from *P. falciparum* (FIG. 22). The pattern is typical for this species and it has been previously described (McCarthy et al., 2013).

Regarding the volatiles, there is a 48 h cycle of increase and decrease in levels of the volatiles before treatment followed by a decrease in levels after treatment (FIG. 22). In this study the inventors did not observe a large initial increase in VOCs directly following treatment which is attributed to the nature of the treatment.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2013904616 filed 28 Nov. 2013, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Aregawi et al. (2011) World Health Organization. Global Malaria Programme. World Malaria Report 2011. Geneva, World Health Organization.
Biamonte et al. (2013) Bioorganic & Medicinal Chemistry Letters 23:2829-2843.
Bloland (2001) Drug resistance in malaria. WHO/CDS/CSR/DRS/2001.4.
Cortes and Vapnik (1995) Mach. Learn. 20(3):273-297.
Dowell and Brown (2009) Methods in Molecular Biology 552:213-229.
Fukutani (2012) Biotechnology and Bioengineering 109: 205-212.
Hanscheid et al. (1999) Clin. Lab. Haem. 21:235-245.
Karunamoorthi (2014) Malaria Journal 13:209.
Le Manach et al. (2013) Malaria Journal 12:424.
Lin CCCCJ (2011) LIBSVM: a library for support vector machines (www.csie.ntu.edu.tw/~cjlin/libsvm).
McCarthy et al. (2011) Plos One. DOI: 10.1371/journal.pone.0021914.
McCarthy et al. (2013) J. Infect. Dis. 208:1688-1694.
Mochalski et al. (201.3) Analyst 138:2134-2145.
Russell and Norvig (1995) Articial Intelligence: A Modern Approach, ed Pentice Hall EC, N.J.
Vaughan (2012) Future Microbiol. 7:657-665.
Wang et al. (2014) PLoS One 9(3):e89840.
Wong et al. (2012) Malaria Journal 11:314.
Wilson (2012) Clinical Infectious Diseases 54:1637-1641.

The invention claimed is:

1. A method for identifying a human subject with a *Plasmodium falciparum* infection, the method comprising detecting one or more volatile organic compounds selected from the group consisting of allyl methyl sulphide, 1-methylthiopropane, (E)-1-methylthio-1-propene, and (Z)-1-methylthio-1-propene, in the subject or a sample obtained therefrom, wherein the levels of the one or more volatile organic compounds indicates a *Plasmodium falciparum* infection.

2. The method of claim 1, wherein the levels of the one or more volatile organic compounds also indicate the status of the *Plasmodium falciparum* infection.

3. The method of claim 1, wherein in the sample is selected from the group consisting of exhaled breath, condensate breath, saliva, blood, sweat, skin microbiota, skin volatile sample and urine.

4. The method of claim 3, wherein the sample is exhaled breath.

5. The method of claim 1 which further comprises comparing the level of the one or more volatile organic compounds to a suitable control.

6. The method of claim 1, wherein the detection or monitoring of the one or more volatile organic compound comprises the use of at least one technique selected from the group consisting of mass spectrometry (MS) (such as gas chromatography mass spectrometry (GCMS), liquid chromatography mass spectrometry (LCMS) and proton transfer reaction mass spectrometry (PTR-MS)); ion mobility spectrometry; field asymmetric ion mobility spectrometry; differential mobility spectrometry (DMS); electronic nose device; biosensor; an antibody-based detection system; colorimetric assays; infrared spectroscopy (IR spectroscopy) (such as near-infrared (NIR), Fourier Transform-Infrared (FTIR) spectroscopy and ring-down cavity spectroscopy); selected ion flow tube mass spectrometry (SIFT), fuel cell electrodes; light absorption spectroscopy; nanoparticle technology; flexural plate wave (FPW) sensors; electrochemical sensors; photoacoustic equipment; laser-based equipment; various ionization techniques and trained animal detection or combinations thereof.

7. The method according to claim 6, wherein the detection or monitoring of the one or more volatile organic compound comprises the use of at least one technique selected from the group consisting of gas chromatography mass spectrometry (GCMS), liquid chromatography mass spectrometry (LCMS), electronic nose device, biosensor, an antibody-based detection system, colorimetric assays, near-infrared (NIR), selected ion flow tube mass spectrometry (SIFT) and proton transfer reaction mass spectrometry (PTR-MS).

8. The method of claim 7, wherein the detection of the one or more volatile organic compound comprises the use of gas chromatography mass spectrometry (GCMS) or an electronic nose device.

\* \* \* \* \*